United States Patent [19]

Zurmühlen et al.

[11] Patent Number: 5,446,013
[45] Date of Patent: Aug. 29, 1995

[54] 2-ALKYL-OR-ARYL-SUBSTITUTED-2-(PYRIMIDINYL-OR-TRAIZINYL-OXY(OR-THIO))-ACOTIC ACID DERIVATIVES, PROCESS FOR PREPARATION, AND USE AS HERBICIDES OR PLANT-GROWTH REGULATORS

[75] Inventors: Frank Zurmühlen, Frankfurt am Main; Klaus Bauer, Hanau; Hermann Bieringer, Eppstein/Taunus, all of Germany

[73] Assignee: Hoechst Aktiengesellschaft, Frankfurt, Germany

[21] Appl. No.: 168,981

[22] Filed: Dec. 17, 1993

Related U.S. Application Data

[63] Continuation of Ser. No. 988,904, Nov. 5, 1992, abandoned.

[30] Foreign Application Priority Data

Nov. 7, 1991 [DE] Germany .................. 41 36 569.0

[51] Int. Cl.⁶ .................. A01N 43/54; C07D 239/42; C07D 239/60
[52] U.S. Cl. .................. 504/242; 504/243; 504/193; 504/197; 544/229; 544/243; 544/300; 544/301; 544/302; 544/310; 544/312; 544/314; 544/316; 544/317; 544/318
[58] Field of Search .......... 504/242, 243, 193; 544/300, 314, 318, 229

[56] References Cited

U.S. PATENT DOCUMENTS

| | | | |
|---|---|---|---|
| 4,968,340 | 11/1990 | Kaku et al. | 504/242 |
| 5,238,934 | 8/1993 | Knuppel et al. | 504/242 |
| 5,387,575 | 2/1995 | Harada et al. | 504/243 |

FOREIGN PATENT DOCUMENTS 0347811 12/1989 European Pat. Off. .
0400741 12/1990 European Pat. Off. .
0411706 2/1991 European Pat. Off. .

OTHER PUBLICATIONS

Chemical Abstracts, vol. 117, 1992, No. 28, Columbus, Ohio, Abstract No. 48615r, "Triazines And Other 6-Membered Rings", p. 943 Harada.

*Primary Examiner*—John M. Ford
*Attorney, Agent, or Firm*—Curtis, Morris & Safford

[57] ABSTRACT

Pyrimidinyl- or triazinyloxy- (or -thio)-carboxylic acid derivatives, processes for their preparation, and their use as herbicides or plant growth regulators Compounds of the formula (I)

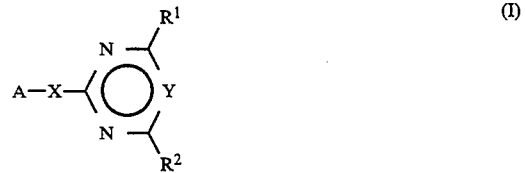

in which

A is

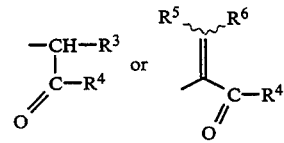

and $R^1$, $R^2$, $R^3$, $R^4$, $R^5$, $R^6$, X and Y are as defined in claim 1 are suitable as selective herbicides and plant growth regulators.

8 Claims, No Drawings

2-ALKYL-OR-ARYL-SUBSTITUTED-2-(PYRIMIDI-NYL-OR-TRAIZINYL-OXY(OR-THIO))-ACOTIC ACID DERIVATIVES, PROCESS FOR PREPARATION, AND USE AS HERBICIDES OR PLANT-GROWTH REGULATORS

This application is a continuation of application Ser. No. 07/988,904, filed Nov. 5, 1992, now abandoned.

It is known that pyrimidinyloxy(thio)- and triazinyloxy(thio)-carboxylic acid derivatives have herbicidal and plant-growth-regulating properties (see EP-A-0,347,811, EP-A-0,409,369 (CA-A-2,021,486), EP-A-0,409,368 (CA-A-2,021,486), EP-A-400,741). However, some of the known active substances of this structural type have disadvantages when used, for example insufficient selectivity in important crops.

Novel pyrimidinyloxy(thio)- and triazinyloxy(thio)-carboxylic acid derivatives which have advantageous herbicidal properties have now been found.

The invention relates to compounds of the formula (I)

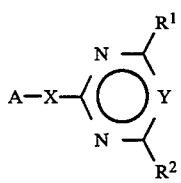
(I)

in which
A is a radical of the formula

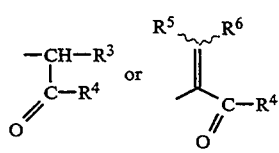

X is O or S,
Y is N or CH,
$R^1$ and $R^2$ independently of one another are hydrogen, alkyl, alkoxy, alkylthio, halogen, haloalkoxy, amino, alkylamino or dialkylamino,
$R^3$ is an aliphatic, araliphatic or aromatic radical of the formula

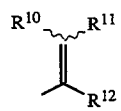

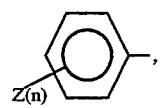

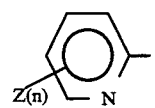

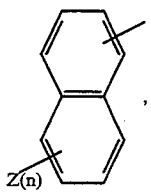

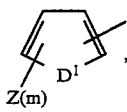

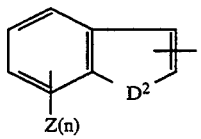

or

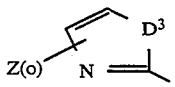

$R^5$ is alkyl, alkenyl or alkynyl, the three last-mentioned radicals independently of one another being unsubstituted or mono- or polysubstituted by radicals selected from the group comprising alkoxy, alkylthio, amino, alkylamino, dialkylamino, nitro, halogen, phenyl and substituted phenyl, or cycloalkyl or cycloalkenyl, the two last-mentioned radicals independently of one another being unsubstituted or mono- or polysubstituted by radicals selected from the group comprising alkyl, alkoxy, alkylthio, amino, alkylamino, dialkylamino, nitro, halogen, phenyl and substituted phenyl or a radical of the formula

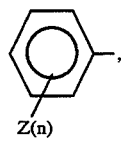

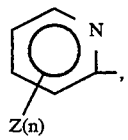

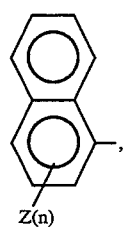

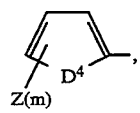

-continued

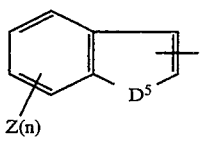

or

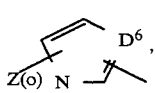

$R^6$ is hydrogen or alkyl, $R^7$ is hydrogen, halogen, alkyl which is unsubstituted or substituted by one or more radicals selected from the group comprising halogen, hydroxyl, alkoxy and alkylthio, or is cycloalkyl, hydroxyl, cyano, thienyl, naphthyl or dihydronaphthyl, the three last-mentioned radicals being unsubstituted or substituted, or is a radical of the formula

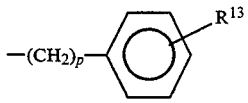

$R^{13}$ is hydrogen, halogen, nitro, alkyl, haloalkyl, alkoxy, alkylsulfonyl, alkylsulfinyl or alkylthio, $R^8$ and $R^9$ independently of one another are hydrogen or alkyl, or $R^8$ and $R^9$ together with the carbon atom linking them form a 3- to 6-membered ring which can contain an oxygen atom and be substituted by one or more alkyl groups, $R^{10}$ radicals independently of one another are hydrogen or alkyl, or $R^{10}$ together with $R^{12}$ and the ethylene group linking them are a cyclopentene or cyclohexene ring which is unsubstituted or substituted by one or more alkyl groups, $R^{11}$ is hydrogen or alkyl, $R^{12}$ is alkyl, phenyl or substituted phenyl, or $R^{12}$ together with $R^{10}$ and the ethylene group linking them are a cyclopentene or cyclohexene ring which is unsubstituted or substituted by one or more alkyl groups, $D^1$ to $D^6$ independently of one another are O, S or $NR^{14}$, $R^{14}$ is hydrogen, alkyl or phenyl, n is an integer from 0 to 4, preferably 0 to 3, m is an integer from 0 to 3, preferably 0 or 1, o is an integer from 0 to 2, preferably 0 or 1, P is an integer from 0 to 2, preferably 0 or 1, Z independently of one another are halogen, alkyl, haloalkyl, alkoxy, haloalkoxy, alkylthio, amino, alkylamino, dialkyl amino, nitro, phenyl or substituted phenyl, $R^4$ is an alkoxy radical which is substituted by alkenyloxy, alkynyloxy, cycloalkyloxy, cyclo alkenyloxy, benzyloxy, benzylthio, $(R^*)_3Si$ or $(R^*)_3SiO$, in which the radicals $R^*$ independently of one another are alkyl, alkenyl or alkynyl, aryl or substituted aryl, or by cyano, nitro, alkylcarbonyl, alkenylcarbonyl, alkynyl carbonyl, cycloalkylcarbonyl, alkylsulfonyl, alkylsulfinyl, dialkylphosphinyl, dialkyl phosphonyl, dialkylphosphoryl, pyridyl or substituted pyridyl, or $R^4$ is the radical of 5- or 6-membered cyclic lactone or $R^4$ is a radical of the formula $$-D^7-CR^{15}R^{16}-D^8-L$$

$$-NR^{32}-SO_2-R^{33}$$

$$-NR^{34}-O-R^{35}$$

$$-NR-N=CR^{21}R^{22} \text{ or}$$

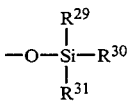

$D^7$ is O, S or $NR^{14}$, $D^8$ is a direct bond or a saturated or unsaturated hydrocarbon group, preferably a direct bond, $CH_2$, $CH(CH_3)$ or $C(CH_3)_2$, $R^{15}$ and $R^{16}$ independently of one another are hydrogen, alkyl, alkenyl, alkynyl, aryl, substituted aryl, benzyl, alkoxy, alkenyloxy, alkynyloxy, aryloxy or substituted aryloxy, L is an acid derivative radical of the formula $$-CO-O-R^{17}$$

$$-CO-S-R^{18}$$

$$-CO-NR^{19}R^{20}$$

$$-CO-O-N=CR^{21}R^{22}$$

$$-CO-N=CR^{21}R^{22}$$

$$-O-CO-R^{23}$$

$$-S-CO-R^{23}$$

$$-NR^{14}-CO-R^{23}$$

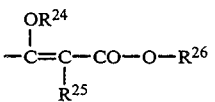

or

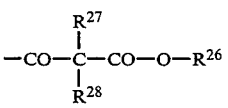

$R^{17}$ and $R^{18}$ are hydrogen, alkyl, alkenyl or alkynyl, the 3 last-mentioned radicals being unsubstituted or substituted by one or more radicals selected from the group comprising halogen, or are cycloalkyl, cycloalkenyl, benzyl, phenyl or substituted phenyl, $R^{19}$ and $R^{20}$ independently of one another are hydrogen, alkyl, alkenyl, alkynyl, cycloalkyl, benzyl, phenyl or substituted phenyl, or together with the nitrogen atom linking them are a heterocyclic 3- to 7-membered ring which, besides the nitrogen atom, can additionally contain hetero atoms selected from the group comprising N, O and S, $R^{21}$ and $R^{22}$ independently of one another are hydrogen, alkyl, alkenyl or alkynyl, or together with the carbon atom linking them are a carbocylic 4- to 8-membered radical, $R^{23}$ is hydrogen, alkyl, cycloalkyl, phenyl or substituted phenyl, $R^{24}$ is alkyl, alkenyl or alkynyl, the 3 last-mentioned radicals being unsubstituted or substituted by one or more radicals selected from the group comprising halogen, alkoxy, alkenyloxy and alkynyloxy, or are cycloalkyl, cycloalkenyl, alkanoyl, alkoxycarbonyl, benzyl, benzoxycarbonyl, phenyl or benzoyl, the 4 last-mentioned radicals being unsubstituted or substituted, $R^{25}$ is hydrogen, alkyl, alkanoyl, alkoxycarbonyl, alkenyloxycarbonyl, alkynyloxycarbonyl, phenyl or substituted phenyl, $R^{26}$ is hydrogen, alkyl, alkenyl or alkynyl, the 3 last-mentioned radicals being unsubstituted or substituted by one or more radicals selected from the group comprising halogen, $R^{27}$ and $R^{28}$ independently of one another are hydrogen, alkyl, alkanoyl, alkoxycarbonyl, alkenyloxycarbonyl, alkynyloxycarbonyl, phenyl or substituted phenyl, $R^{29}$, $R^{30}$ and $R^{31}$ independently of one another are alkyl, alkenyl or alkynyl, phenyl or substituted phenyl, $R^{32}$ is hydrogen, alkyl, alkenyl, alkynyl, aryl or aralkyl, $R^{33}$ is alkyl, aryl, substituted aryl, aralkyl or substituted aralkyl, $R^{34}$ is hydrogen, alkyl, alkenyl, alkynyl, aryl or aralkyl and $R^{35}$ is hydrogen, alkyl, alkenyl, alkynyl, aryl or aralkyl.

In formula (I) and hereinafter, the radicals alkyl, alkoxy, haloalkyl, haloalkoxy, alkylamino and alkylthio and the corresponding unsaturated and/or substituted radicals can in each case be straight-chain or branched. Unless specifically indicated, preferred radicals are those where the carbon atom chains or carbon skeletons have 1 to 4 carbon atoms, or, in the case of unsaturated groups, 2 to 4 carbon atoms. Alkyl radicals, also in the composite meanings such as alkoxy, haloalkyl and the like, are methyl, ethyl, n- or i-propyl, n-, i-, t- or 2-butyl; alkenyl and alkynyl radicals have the meaning of the unsaturated radicals which are possible and which correspond to the alkyl radicals, such as 2-propenyl, 2- or 3-butenyl, 2-propynyl, and 2- or 3-butynyl. Halogen is fluorine, chlorine, bromine or iodine, haloalkyl is alkyl which is substituted by one or more atoms selected from the group comprising halogen; haloalkyl is, for example, $CF_3$, $CHF_2$, $CH_2CF_3$. The same applies analogously to haloalkenyl, haloalkoxy and other halogen-substituted radicals. Aryl is, for example, phenyl, naphthyl, tetrahydronaphthyl, indenyl, indanyl, pentalenyl, fluorenyl and the like, preferably phenyl; aryloxy denotes the corresponding oxy radicals, preferably phenoxy. Heteroaryl, or heteroaryl in heteroaryloxy, denotes, for example, pyridyl, pyrimidyl, pyridazyl, thienyl, furyl, pyrrolyl, pyrazolyl and imidazolyl, preferably pyridyl and thienyl, but also bicyclic or polycyclic aromatic or araliphatic compounds. Optionally substituted aryl, aryloxy, heteroaryl, hetaryloxy, phenyl, phenoxy, benzyl and benzyloxy as well as bicyclic radicals having aromatic moieties preferably denote in each case the corresponding unsubstituted radical or denote a substituted radical derived therefrom, the substituents being, for example, one or more, preferably 1, 2 or 3, radicals selected from the group comprising halogen, alkyl, haloalkyl, alkoxy, haloalkoxy, nitro, cyano, alkoxycarbonyl, alkylcarbonyl, alkanoyl, carbamoyl, mono- and dialkylaminocarbonyl, mono- and dialkylamino, alkylsulfinyl and alkylsulfonyl and, in the case of radicals having carbon atoms, those having 1 to 4 carbon atoms, in particular 1 or 2, are preferred. Preferred substituents are, as a rule, those selected from the group comprising halogen, such as fluorine or chlorine, $C_1$-$C_4$-alkyl, preferably methyl or ethyl, $C_1$-$C_4$-haloalkyl, preferably trifluoromethyl, $C_1$-$C_4$-alkoxy, preferably methoxy or ethoxy, $C_1$-$C_1$-haloalkoxy, nitro and cyano. Methyl, methoxy and chlorine are particularly preferred.

Examples of silicon-containing radicals $R^4$ are trialkylsilylalkoxy, aryldialkylsilylalkoxy, diarylalkylsilylalkoxy, trialkylsilylalkenyloxy, aryldialkylsilylalkenyloxy, diarylalkylsilylalkenyloxy, trialkylsilylalkynyloxy, aryldialkylsilylalkynyloxy, diarylalkylsilylalkynyloxy, trialkylsilyloxy, aryldialkylsilyloxy, diarylalkylsilyloxy.

The invention also relates to all stereoisomers and their mixtures which come under the formula (I) but are not specifically defined.

Particularly interesting compounds of the formula (I) according to the invention are those in which $R^1$, $R^2$ independently of one another are $C_1$-$C_1$-alkyl, $C_1$-$C_1$-alkoxy, halogen, $C_1$-$C_1$-haloalkoxy, $C_1$-$C_1$-alkylamino or di-($C_1$-$C_1$-alkyl)amino, preferably methyl, methoxy, chlorine or methylamino, in particular one of the two radicals being methoxy and the other radical being methyl, methoxy, chlorine or methylamino.

Other compounds of the formula (I) according to the invention which are of particular interest are those in which A is a radical of the formula —$CHR^3$—CO—$R^4$, $R^3$ is an aliphatic, araliphatic or aromatic radical of the formula —$CR^7R^8R^9$ or phenyl, pyridyl or thienyl, where the 3 last-mentioned radicals are unsubstituted or substituted by 1 to 3 radicals Z, $R^7$ is hydrogen, halogen, $C_1$-$C_4$-alkyl, phenyl or benzyl, preferably hydrogen or methyl, $R^8$ and $R^9$ independently of one another are hydrogen or $C_1$-$C_4$-alkyl, or $R^8$ and $R^9$ together with the carbon atom linking them are a 5- or 6-membered ring and Z independently of one another are halogen, $C_1$-$C_4$-alkyl, $C_1$-$C_4$-haloalkyl, $C_1$-$C_4$-alkoxy, $C_1$-$C_4$-haloalkoxy, $C_1$-$C_4$alkylthio, $C_1$-$C_4$-alkylamino, di-($C_1$-$C_4$-alkyl) amino or nitro.

$R^3$ is preferably isopropyl, 2,2-dimethyl-ethyl or cyclopentyl.

Other compounds of the formula (I) according to the invention which are of particular interest are those in which A is a radical of the formula

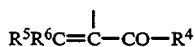

$R^5$ is $C_1$-$C_4$-alkyl, $C_2$-$C_1$-alkenyl or $C_2$-$C_4$-alkynyl, cyclohexyl, cyclopentyl, phenyl, pyridyl or thienyl, where the 3 last-mentioned radicals are unsubstituted or substituted by 1 to 3 radicals Z, $R^6$ is hydrogen or $C_1$-$C_4$-alkyl and Z independently of one another are halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylamino, di-($C_1$-$C_4$-alkyl)amino or nitro.

Other compounds of the formula (I) according to the invention which are of particular interest are those in which $R^4$ is a $C_1$-$C_4$-alkoxy radical which is substituted by $C_2$-$C_1$-alkenyloxy, $C_2$-$C_4$-alkynyloxy, cyclohexyloxy, cyclohexenyloxy, cyclopentyloxy, cyclopentenyloxy, benzyloxy, benzylthio, (R*)$_3$Si or (R*)$_3$SiO, in which the radicals R* independently of one another are C$_1$–C$_4$-alkyl, C$_2$–C$_4$-alkenyl, C$_2$–C$_4$-alkynyl or phenyl, or by cyano, nitro, (C$_1$–C$_4$-alkyl)-carbonyl, C$_1$–C$_4$-alkylsulfonyl, C$_1$–C$_4$-alkylsulfinyl, di-(C$_1$–C$_4$-alkyl)-phosphinyl, di-(C$_1$–C$_1$-alkyl)-phosphonyl, di-(C$_1$–C$_1$-alkyl)-phosphoryl or pyridyl, or R$^4$ is the radical of a 5- or 6-membered cyclic lactone bonded to the remaining moiety in the α-position relative to the carbonyl group, or R$^4$ is a radical of the formula

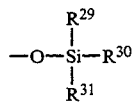

D$^7$ is O, S, NH, methylamino or ethylamino,

D$^8$ is a direct bond,

R$^{15}$ and R$^{16}$ independently of one another are hydrogen, C$_1$–C$_1$-alkyl, C$_2$–C$_4$-alkenyl, C$_2$–C$_4$-alkynyl, phenyl or benzyl, preferably hydrogen or methyl, L is an acid derivative radical of the formula

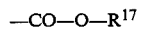

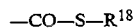

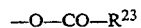

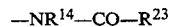

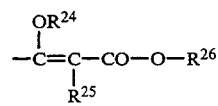

or

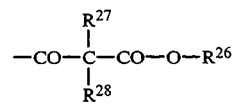

R$^{17}$ is hydrogen, C$_2$–C$_4$-alkenyl or C$_2$–C$_4$-alkynyl, cyclohexyl, cyclopentyl, cyclohexenyl, cyclopentenyl, benzyl, phenyl or substituted phenyl, R$^{18}$ is hydrogen, C$_1$–C$_4$-alkyl, C$_2$–C$_1$-alkenyl or C$_2$–C$_4$-alkynyl, cyclohexyl, cyclopentyl, cyclohexenyl, cyclopentenyl, benzyl, phenyl or substituted phenyl, R$^{19}$ and R$^{20}$ independently of one another are hydrogen, C$_1$–C$_4$-alkyl, C$_2$–C$_4$-alkenyl, C$_2$–C$_4$-alkynyl, cyclohexyl, cyclopentyl, benzyl, phenyl or substituted phenyl, or, together with the nitrogen atom linking them, a heterocyclic 5- or 6-membered ring which, besides the nitrogen atom, can additionally contain an oxygen atom as hetero atom, R$^{21}$ and R$^{22}$ independently of one another are C$_1$–C$_4$-alkyl, C$_2$–C$_1$-alkenyl or C$_2$–C$_4$-alkynyl or, together with the carbon atom linking them, a carbocylic 5- to 6-membered radical, R$^{23}$ is hydrogen, C$_1$–C$_4$-alkyl, cyclohexyl, cyclopentyl, phenyl or substituted phenyl, R$^{24}$ is C$_1$–C$_4$-alkyl, C$_2$–C$_4$-alkenyl or C$_2$–C$_4$-alkynyl, where the 3 last-mentioned radicals are unsubstituted or substituted by one or more radicals selected from the group comprising halogen or C$_1$–C$_4$-alkoxy, or is C$_1$–C$_4$-alkanoyl, (C$_1$–C$_4$-alkoxy)-carbonyl, benzyl, benzoxycarbonyl, phenyl or benzoyl, the 4 last-mentioned radicals being unsubstituted or substituted by C$_1$–C$_4$-alkyl, C$_1$–C$_4$-alkoxy, halogen or nitro, R$^{25}$ is hydrogen or C$_1$–C$_4$-alkyl, R$^{26}$ is hydrogen, C$_1$–C$_4$-alkyl, C$_2$–C$_4$-alkenyl or C$_2$–C$_4$-alkynyl, where the 3 last-mentioned radicals are unsubstituted or substituted by one or more radicals selected from the group comprising halogen, R$^{27}$, and R$^{28}$ independently of one another are hydrogen or C$_1$–C$_4$-alkyl and R$^{29}$, R$^{30}$ and R$^{31}$ independently of one another are C$_1$–C$_4$-alkyl, C$_2$–C$_4$-alkenyl or C$_2$–C$_4$-alkynyl, phenyl or substituted phenyl.

Preferred compounds of the formula (I) according to the invention are those in which R$^4$ is a C$_1$–C$_4$-alkoxy radical which is substituted by allyl, propargyl, (R*)$_3$Si or (R*)$_3$SiO, in which the radicals R* independently of one another are methyl, ethyl or phenyl, or by cyano, C$_1$–C$_4$-alkylsulfonyl, C$_1$–C$_4$-alkylsulfinyl, di-(C$_1$–C$_4$-alkyl)-phosphinyl, di-(C$_1$–C$_4$-alkyl)-phosphonyl, di-(C$_1$–C$_4$-alkyl)-phosphoryl or pyridyl, or R$^4$ is the radical of a 5-membered cyclic lactone bonded to the remaining moiety in the α-position relative to the carbonyl group, or R$^4$ is a radical of the formula

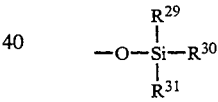

D$^7$ is O, S or NH,

D$^8$ is a direct bond,

R$^{15}$ and R$^{16}$ independently of one another are hydrogen or methyl,

L is an acid derivative radical of the formula

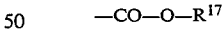

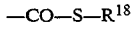

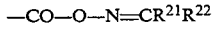

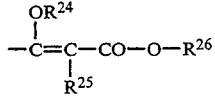

or

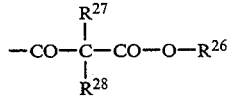

$R^{17}$ is hydrogen, $C_2$-$C_4$-alkenyl or $C_2$-$C_4$-alkynyl, benzyl or phenyl, $R^{18}$ is hydrogen, $C_1$-$C_4$-alkyl, $C_2$-$C_4$-alkenyl or $C_2$-$C_4$-alkynyl, benzyl or phenyl, $R^{19}$ and $R^{20}$ independently of one another are hydrogen, $C_1$-$C_4$-alkyl, $C_2$-$C_4$-alkenyl, $C_2$-$C_4$-alkynyl, cyclohexyl, cyclopentyl, benzyl, phenyl or substituted phenyl, or, together with the nitrogen atom linking them, a heterocyclic 5- or 6-membered ring which, besides the nitrogen atom, can additionally contain an oxygen atom as hetero atom, $R^{24}$ is $C_1$-$C_4$-alkyl where the last-mentioned radical is unsubstituted or substituted by one or more radicals selected from the group comprising halogen or $C_1$-$C_4$-alkoxy, or is $C_1$-$C_4$-alkanoyl, ($C_1$-$C_4$-alkoxy)-carbonyl, benzyl, benzoxycarbonyl, phenyl or benzoyl, where the 4 last-mentioned radicals are unsubstituted or substituted by $C_1$-$C_4$-alkyl, $C_1$-$C_4$-alkoxy, halogen or nitro, $R^{25}$ is hydrogen or $C_1$-$C_4$-alkyl, $R^{26}$ is hydrogen, $C_1$-$C_4$-alkyl, $C_2$-$C_4$-alkenyl or $C_2$-$C_4$-alkynyl, $R^{27}$ and $R^{28}$ independently of one another are hydrogen or $C_1$-$C_4$-alkyl and $R^{29}$, $R^{30}$ and $R^{31}$ independently of one another are $C_1$-$C_4$-alkyl, $C_2$-$C_4$-alkenyl or $C_2$-$C_4$-alkynyl or phenyl.

Other preferred compounds of the formula (I) according to the invention are those in which the individual radicals and groups contain two or more of the radicals or groups mentioned above as being preferred.

The present invention furthermore relates to the process for the preparation of compounds of the formula I, which comprises (a) if A is a radical of the formula —$CHR^3$—CO—$R^4$, reacting a compound of the formula (II)

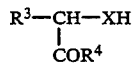

in which $R^3$, $R^4$ and X are as defined in formula (I), with a compound of the formula (III)

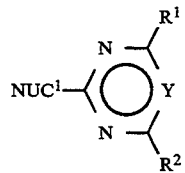

in which $NUC^1$ is a leaving group, for example selected from the group comprising halogen, alkylsulfonyl, benzylsulfonyl and substituted benzylsulfonyl, and $R^1$, $R^2$ and Y are as defined in formula (I), in the presence of an inorganic or organic base, (b) if A is a radical of the formula —$CHR^3$—CO—$R^4$, reacting a compound of the formula (IV)

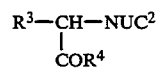

in which $NUC^2$ is a leaving group, for example selected from the group comprising halogen and methylsulfonyloxy, and $R^3$ and $R^4$ are as defined in formula (I), with a compound of the formula (V)

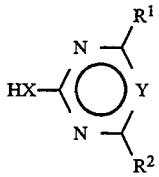

in which $R^1$, $R^2$, X and Y are as defined in formula (I), in the presence of an inorganic or organic base, (c) if A is the group

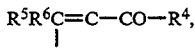

reacting a compound of the formula (VI)

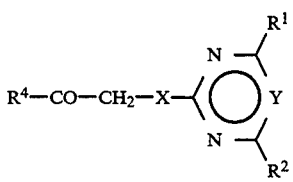

in which $R^1$, $R^2$, $R^4$, X and Y are as defined in formula (I), with an aldehyde or ketone of the formula (VII)

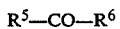

in which $R^5$ and $R^6$ are as defined in formula (I), in the presence of a suitable inorganic or organic base, (d) if A is a radical of the formula —CH$R^3$—CO—$R^4$, reacting a compound of the formula (VI) mentioned under (c) with a halogen compound of the formula (VIII)

in which Hal is chlorine, bromine or iodine and $R^3$ is as defined in formula (I), in the presence of an inorganic or organic base, or (e) reacting a compound of the formula (IX) or (X)

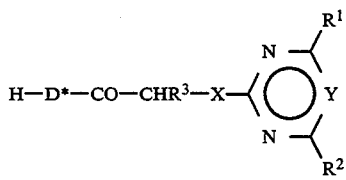

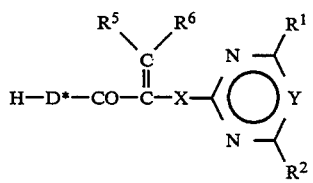

in which $R^1$, $R^2$, $R^3$, $R^5$, $R^6$, X and Y are as defined in formula (I) and D* is O, S or $NR^{14}$ where $R^{14}$ is H, alkyl or phenyl, with a halogen compound of the formula (XI)

in which R° is defined such that R°—D*— has the meaning of $R^4$ in formula (I), in the presence of an inorganic or organic base, or (f) reacting a compound of the formula (IX) or (X) in which D* is an oxygen atom with thionyl chloride, oxalyl chloride, chlorocarbonate, carbonyldiimidazole or dicyclohexylcarbodiimide/4-N,N-dimethyl aminopyridine in a manner known per se to give an activated carboxylic acid derivative, and reacting the latter with a compound of the formula (XII)

$$R^4—H$$

in the presence of an inorganic or organic base.

Bases which are suitable for the reactions (a) to (e) are, for example, inorganic bases from the group comprising the alkali metal carbonates, such as $Na_2CO_3$, $K_2CO_3$, $NaHCO_3$ or $KHCO_3$, alkali metal hydrides, such as NaH and KH, and alkali metal fluoride, such as KF, or organic bases such as triethylamine or DBU (1,8-diazabicyclo[5.4.0]undec-7-ene).

As a rule, it is expedient to carry out these reactions in the presence of a solvent, for example using a solvent such as toluene, xylene, diethylethane, diglyme, monoglyme, tetrahydrofuran, dioxane, dimethylformamide, N,N-dimethylacetamide, dimethyl sulfoxide or acetonitrile.

It can also be advantageous to carry out the reactions in the presence of catalysts, for example crown ethers or N,N,N',N', -tetramethylenediamine Suitable bases for reaction (f) are, for example, alkali metals such as sodium or potassium, alkali metal carbonates, such as $K_2CO_3$, $Na_2CO_3$, $NaHCO_3$ or $KHCO_3$, alkali metal hydrides and alkaline earth metal hydrides such as NaH, KH or $CaH_2$, alkali metal hydroxides such as KOH or NaOH, or organic bases such as triethylamine. Solvents which can be employed in this reaction are hydrocarbons such as n-heptane, benzene, toluene or xylene, halogenated hydrocarbons such as $CH_2Cl_2$, $CHCl_3$, $CCl_4$ and chlorobenzene, alcohols such as $CH_3OH$, $C_2H_5OH$ or 2-propanol, ethers such as diethyl ether, dioxane and tetrahydrofuran (THF), ketones such as acetone or methyl ethyl ketone, esters such as ethyl acetate, aprotic polar solvents such as dimethylformamide (DMF), N,N-dimethylacetamide, dimethyl sulfoxide (DMSO), acetonitrile and water.

The starting materials of the formulae II-XII are known or can be synthesized analogously to known processes (cf. literature: EP-A-347,811, EP-A-409,369 (CA-A-2,021,486), EP-A-409,368 (CA-A-2,021,486), EP-A-400,741).

The compounds of the formula (I) according to the invention have an excellent herbicidal activity against a broad range of economical important monocotyledon and dicotyledon harmful plants. The active substances also act efficiently on perennial weeds which produce shoots from rhizomes, rootstocks or other perennial organs and which are difficult to control. In this context, it does not matter whether the substances are applied before sowing, pre-emergence or post-emergence.

Specifically, examples may be mentioned of some representatives of the monocotyledon and dicotyledon weed flora which can be controlled by the compounds according to the invention, without these being a restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledon weed species, the range of action extends to species such as, for example, Galium, Viola, Veronica, Lamium, Stellaria, Amaranthus, Sinapis, Ipomoea, Matricaria, Abutilon and Sida from amongst the annuals, and to Convolvulus, Cirsium, Rumex and Artemisia in the case of the perennial weeds.

The active substances according to the invention equally effect outstanding control of weeds which occur under the specific conditions of rice growing such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage but then their growth stops, and, eventially, after three or four weeks have elapsed, they die completely.

If the active substances are applied post-emergence to the green parts of the plants, growth equally stops drastically a very short time after the treatment and the weed plants remain at the growth stage of the time of application, or they die completely after a certain time, so that in this manner competition by the weeds, which is harmful to the crop plants, is eliminated at a very early stage and in a sustained manner.

Although the compounds according to the invention have an excellent herbicidal activity against mono- and dicotyledon weeds, crop plants of economically important crops such as, for example, wheat, barley, rye, rice, maize, sugarbeet, cotton and soya, are not damaged at all, or only to a negligible extent. For these reasons, the present compounds are highly suitable for selectively controlling undesired plant growth in plantings for agricultural purposes.

In addition, the substances according to the invention have excellent growth-regulating properties in crop plants. They engage in the plant metabolism in a regulating manner and can thus be employed for the targeted control of plant constituents and for facilitating harvesting, such as, for example, by provoking desiccation and stunted growth. Furthermore, they are also suitable for generally regulating and inhibiting undesired vegetative growth without simultaneously destroying the plants. Inhibition of the vegetative growth plays an important role in many monocotyledon and dicotyledon crops because lodging can be hereby reduced, or prevented completely.

The compounds according to the invention can be applied in the form of wettable powders, emulsifiable concentrates, sprayable solutions, dusts or granules, in the conventional preparations.

The compounds of the formula (I) can be formulated in various ways, depending on the prevailing biological and/or chemicophysical parameters. Examples of possible formulations which are suitable are: wettable powders (WP), emulsifiable concentrates (EC), concentrated emulsions (EW), for example oil-in-water or water-in-oil emulsions, sprayable solutions or emulsions, dispersions on an oil or water basis (SC), dusts (DP), seed-dressing agents, granules (G) such as granules for soil application and for broadcasting (FG), water-dispersible granules (WDG), ULV formulations, microcapsules or waxes.

These individual formulation types are known in principle and are described, for example, in: Winnacker-Küchler, "Chemische Technologie" [Chemical Technology], Volume 7, C. Hauser Verlag Munich, 4th Ed. 1986; van Valkenburg, "Pesticides Formulations", Marcel Dekker N.Y., 2nd Ed. 1972–73; K. Martens, "Spray Drying Handbook", 3rd Ed. 1979, G. Goodwin Ltd. London.

The necessary formulation auxiliaries such as inert materials, surfactants, solvents and other additives are also known and described, for example in: Watkins, "Handbook of Insecticide Dust Diluents and Carriers", 2nd Ed., Darland Books, Caldwell N.J.; H. V. Olphen, "Introduction to Clay Colloid Chemistry"; 2nd Ed. J. Wiley and Sons, N.Y.; Marsden, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "GrenzfläMchenaktive Äthylenoxidaddukte" [Surface-Active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Wettable powders are preparations which are uniformly dispersible in water and which, besides the active substance and a diluent or inert substance, also contain wetting agents, for example polyoxyethylated alkylphenols, polyoxethylated fatty alcohols, alkane- or alkylarylsulfonates and fatty alcohol polyglycol ether sulfates, and dispersing agents, for example sodium ligninsulfonates, sodium 2,2'-dinaphthylmethane-6,6'-disulfonate, sodium dibutylnaphthalinesulfonate, or else sodium oleylmethyltaurinate.

Emulsifiable concentrates can be prepared by dissolving the active substance in an organic solvent, for example cyclohexanone, xylene or else higher-boiling aromatics or hydrocarbons, with the addition of one or more emulsifiers. Emulsifiers which can be used are, for example: calcium salts of alkylarylsulfonic acids, such as calcium dodecylbenzenesulfonate, fatty alcohol polyglycol ether sulfates or non-ionic emulsifiers such as fatty acid polyglycol esters, alkylaryl polyglycol ethers, fatty alcohol polyglycol ethers, propylene oxide/ethylene oxide condensation products (for example block polymers), fatty alcohol/propylene oxide/ethylene oxide condensation products, sorbitan fatty acid esters, polyoxyethylene sorbitan fatty acid esters or polyoxyethylene sorbitol esters.

Dusts are obtained by grinding the active substance with finely divided solid substances, for example talc, natural clays, such as kaolin, bentonite and pyrophylite, or diatomaceous earths.

Granules such as granules for soil application or broadcasting, or water-dispersible granules, can be produced either by spraying the active substance onto adsorptive, granulated inert material or by applying active substance concentrates onto the surface of carriers such as sand, kaolinites or granulated inert material by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Plate granules, fluidized-bed granules, extruded granules and spray granules can be produced by the customary processes; see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8–57.

For further information on the formulation of crop protection agents see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations contain 0.1 to 99 percent by weight, in particular 0.1 to 95% by weight, of active substance of the formula (I).

In wettable powders, for example, the active substance concentration is approximately 10 to 90% by weight; the remainder to 100% is composed of customary formulation components. In the case of emulsifiable concentrates, the active substance concentration can be approximately 1 to 80, preferably 5 to 80, % by weight. Formulations in the form of dusts contain 1 to 30, preferably, in most cases, 5 to 20, % by weight of active substance, sprayable solutions approximately 0.2 to 25, preferably 2 to 20, % by weight of active substance. In the case of water-dispersible granules, the active substance content depends partly on whether the active compound is in solid or liquid form and on which granulation auxiliaries, fillers etc., are used.

In general, the content in the case of the water-dispersible granules is between 10 and 90% by weight.

In addition, the active substance formulations mentioned contain, if appropriate, the adhesives, wetting agents, dispersing agents, emulsifiers, penetrants, solvents, fillers or carriers which are conventional in each case.

Based on these formulations, it is also possible to prepare combinations with other pesticidally active substances, fertilizers and/or growth regulators, for example in the form of a readymix or a tank mix. Examples of active substances which can be used as components in the combinations with the active substances according to the invention are known active substances as are described, for example, in Weed Research 26, 441–445 (1986), or "The Pesticide Manual", 9th edition, The British Crop Protection Council, 1990/91, Bracknell, England, and in the literature cited therein. The following active substances may be mentioned, for example, as herbicides which are known from the literature and which can be combined with the compounds of the formula (I) (note: either the "common name" of the International Organization for Standardization (ISO) or the chemical name of the compounds is mentioned, if appropriate together with a customary code number): acetochlor; acifluorfen; aclonifen; AKH 7088, i.e. [[[1-[5-[2-chloro-4-(trifluoromethyl)-phenoxy]-2-nitrophenyl]-2-methoxyethylidene]-amino]-oxy]-acetic acid and methyl [[[1-[5-[2-chloro-4-(trifluoromethyl)-phenoxy]-2-nitrophenyl]-2-methoxyethylidene]-amino]-oxy]-acetate; alachlor; alloxydim; ametryn; amidosulfuron; amitrol; AMS, i.e. ammonium sulfamate; anilofos; asulam; atrazin; aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl;

benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; carbetamide; CDAA, i.e. 2-chloro-N,N-di-2-propenylacetamide; CDEC, i.e. 2-chloroallyl diethyldithiocarbamate; CGA 184927, i.e. 2-[4-[(5-chloro-3-fluoro-2-pyridinyl)oxy]phenoxy]-propanoic acid and its 2-propynyl ester; chlomethoxyfen; chloramben; chlorazifop-butyl, pirifenopbutyl; chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clomazone; clomeprop; cloproxydim; clopyralid; cyanazine; cycloate; cycloxydim; cycluron; cyperquat; cyprazine; cyprazole; 2,4-DB; dalapon; desmediphan; desmetryne; di-allate; dicamba; dichlobenil; dichlorprop; diclofop-methyl; diethatyl; difenoxuron; difenzoquat; diflufenican; dimefuron; dimethachlor; dimethametryn; dimethazone, clomazon; dimethipin; dimetrasulfuron, cinosulfuron; dinitramine; dinoseb; dinoterb; dephenamid; dipropetryne; diquat; dithiopyr; diuron; DNOC; eglinazine-ethyl; EL 177, i.e. 5-cyano-1-(1,1-dimethylethyl)-N-methyl-3H-pyrazole-4-carboxamide; endothal; EPTC; esprocarb; ethalflura-lin; ethametsulfuron-methyl; ethidimuron; ethiozine; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; F6285, i.e. 1-[5-(N-methylsulfonyl)amino-2,4-dichlorophenyl]-3-methyl-4-difluoromethyl-1,2,4-triazol-5-one; fenoprop; fenoxan, s. clomazon; fenoxaprop-ethyl; fenuron; flamprop-methyl; flazasulfuron; fluazifop and its ester derivatives; fluchloralin; flumetsulam; N-[2,6-difluorophenyl]-5-methyl-(1,2,4)-triazolo[1,5a]pyrimidine-2-sulfonamide; flumeturon; flumipropyn; fluorodifen; fluoroglycofen-ethyl; fluridone; flurochloridone; fluroxypyr; flurtamone; fomesafen; fosamine; furyloxyfen; glufosinate; glyphosate; halosafen; haloxyfop and its ester derivatives; hexazinone; Hw 52, i.e. N-(2,3-dichlorophenyl)-4-(ethoxymethoxy)benzamide; imazamethabenzmethyl; imazapyr; imazaquin; imazethamethapyr; imazethapyr; imazosulfuron; ioxynil, isocarbamide; isopropalin; isoproturon; isouron; isoxaben; isoxapyrifop; karbutilate; lactofen; lenacil; linuron; MCPA; MCPB; mecoprop; mefenacet; mefluidid, metamitrol; metazachlor; methabenzthiazuron; metham; methazole; methoxyphenone; methyldymron; metobromuron; metolachlor; metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nittalin; nitrofen; nitrofluorfen; norflurazon; orbencarb; oryzalin; oxadiazon; oxyfluorfen; paraquat; pebulate; pendimethalin; perfluidone; phenmedipham; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil, propaquizafop and its ester derivatives; propazine; propham; propyzamide; prosulfalin; prosulfocarb; prynachlor; pyrazolinate; pyrazon; pyrazosulfuron-ethyl; pyrazoxyfen; pyridate; quinchlorac; quinmerac; quinofop and its ester derivatives, quizaolofop and its ester derivatives, quizalofop-ethyl; quizalofop-p-tefuryl; renriduron; dymron; S 275, i.e. 2-[4-chloro-2-fluoro-5-(2-propynyloxy)-phenyl]-4,5,6,7-tetrahydro-2H-indazole; S 482, i.e. 2-[7-fluoro-3,4-dihydro-3-oxo-4-(2-propynyl)-2H-1,4-benzoaxazin-6-yl]-4,5,6,7-tetrahydro-1H-isoindole-1,3(2H)-dione; secbumeton; sethoxydim; siduron; simazine; simetryn; SN 106279, i.e. 2-[[7-[2-chloro-4-(trifluoro-methyl)-phenoxy]-2-naphthalenyl]-oxy]propanoic acid and its methyl ester; sulfometuron-methyl; sulfazuron; flazasulfuron; TCA; tebutam; tebuthiuron; terbacil; terbucarb; terbuchlor; terbumeton; terbuthylazine; terbutryn; TFH 450, i.e. N,N-diethyl-3-[(2-ethyl-6-methylphenyl)-sulfonyl]-1H-1,2,4-triazole-1-carboxamide; thiazafluron; thifensulfuron-methyl; thiobencarb; tiocarbazil; tralkoxydim; tri-allate; triasulfuron; triazofenamide; tribenuron-methyl; triclopyr; tridiphane; trietazine; trifluralin; trimeturon; vernolate; WL 110547, i.e. 5-phenoxy-1-[3-(trifluoromethyl)-phenyl]-1H-tetrazole.

For use, the formulations present in commercially available form are diluted, if appropriate, in a conventional manner, for example using water in the case of wettable powders, emulsifiable concentrates, dispersions and water-dispersible granules. Preparations in the form of dust and granules for soil application or broadcasting and also sprayable solutions are usually not diluted with other inert substances before use.

The application rate of the compounds of the formula (I) required varies with the external conditions, such as temperature, humidity, and the nature of the herbicide used, amongst other factors. It can vary within wide limits, for example between 0,005 and 10.0 kg/ha or more of active ingredient, but it is preferably between 0.01 and 5 kg/ha.

FORMULATION EXAMPLES a) A dust is obtained by mixing 10 parts by weight of a compound of the formula (I) and 90 parts by weight of talc as inert substance, and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium ligninsulfonate and 1 part by weight of sodium oleoylmethyltaurinate as wetting and dispersion agent, and grinding the mixture on a pinned-disk mill.

c) A dispersion concentrate which is readily dispersible in water is obtained by mixing 20 parts by weight of a compound of the formula (I) with 6 parts by weight of alkylphenol polyglycol ether ( ®Triton X 207), 3 parts by weight of isotridecanol polyglycol ether (8 EO) and 71 parts by weight of paraffinic mineral oil (boiling range for example approximately 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexane as solvent and 10 parts by weight of oxethylated nonylphenol as emulsifier.

e) Water-dispersible granules are obtained by mixing 75 parts by weight of a compound of the formula (I),
10 parts by weight of calcium ligninsulfonate,
5 parts by weight of sodium lauryl sulfate, -continued

| | |
|---|---|
| 3 parts by weight | of polyvinyl alcohol and |
| 7 parts by weight | of kaolin, | grinding the mixture in a pinned-disk mill and granulating the powder in a fluidized bed by spraying on water as granulation liquid.

f) Water-dispersible granules are also obtained by homogenizing and precomminuting

| | |
|---|---|
| 25 parts by weight | of a compound of the formula (I), |
| 5 parts by weight | of sodium 2,2'-dinaphthylmethane-6,6'-disulfonate, |
| 2 parts by weight | of sodium oleoylmethyltaurinate, |
| 1 part by weight | of polyvinyl alcohol, |
| 17 parts by weight | of calcium carbonate and |
| 50 parts by weight | of water | in a colloid mill, subsequently grinding the mixture in a bead mill and atomizing and drying the resulting suspension in a spray tower by means of a single-substance nozzle.

CHEMICAL EXAMPLES (Benzyloxycarbonyl)methyl 2-(4,6-dimethoxypyrimidinyl-2-oxy)-3-methylbutanoate (Ex. 61)

0.91 g (15.6 mmol) of potassium fluoride is added with stirring at room temperature to a solution of 4 g (15.6 mmol) of 2-(4,6-dimethoxypyrimidinyl-2-oxy)-3-methylbutanoic acid and 3.58 g (15.6 mmol) of benzyl bromoacetate in 25 ml of dimethylformamide. After stirring at 90° C. for 10 hours, the reaction solution is poured into ice-water and the mixture is extracted with ethyl acetate. Evaporation on a rotary evaporator yields 5.19 g of the title compound (Ex. 61) in the form of a colorless oil.

(Trimethylsilyl)methyl 2-(4,6-dimethoxypyrimidinyl-2-oxy)-3-methylbutanoate (Ex. 391)

2.41 g (11.7 mmol) of dicyclohexylcarbodiimide are added dropwise with stirring at 20° C. to a solution of 3 g (11.7 mmol) of 2-(4,6-dimethoxypyrimidinyl-2-oxy)-3-methylbutanoic acid, 1.22 g (11.7 mmol) of trimethylsilylmethanol and 0.05 g of 4-dimethylaminopyridine in 25 ml of $CH_2Cl_2$. After stirring at room temperature for 12 hours followed by column filtration, 2.9 g of the title compound (Ex. 391) are obtained in the form of a colorless oil.

The remaining compounds of Table I below are obtained analogously to the above-described examples and process variants.

TABLE I

Compounds of the formula Ia

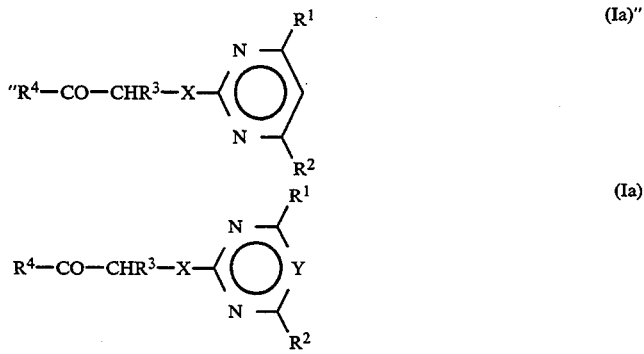

| Ex. No. | $R^1$ | $R^2$ | X | Y | $R^3$ | $R^4$ | m.p.(°C.) or $[n]_D^{20}$ |
|---|---|---|---|---|---|---|---|
| 1 | $OCH_3$ | $OCH_3$ | O | CH | $i-C_3H_7$ | $OCH_2COOCH_2CH=CH_2$ | 52 |
| 2 | Cl | " | " | " | " | " | |
| 3 | $CH_3$ | " | " | " | " | " | |
| 4 | $NHCH_3$ | " | " | " | " | " | |
| 5 | $OCH_3$ | " | S | " | " | " | |
| 6 | Cl | " | " | " | " | " | |
| 7 | $CH_3$ | " | " | " | " | " | |
| 8 | $NHCH_3$ | " | " | " | " | " | |
| 9 | $OCH_3$ | " | " | N | " | " | |
| 10 | " | " | O | " | " | " | |
| 11 | " | " | " | CH | $t-C_4H_9$ | " | |
| 12 | Cl | " | " | " | " | " | |
| 13 | $CH_3$ | " | " | " | " | " | |
| 14 | $NHCH_3$ | " | " | " | " | " | |
| 15 | $OCH_3$ | " | " | " | " | " | |
| 16 | Cl | " | " | " | " | " | |
| 17 | $CH_3$ | " | " | " | " | " | |
| 18 | $NHCH_3$ | " | " | " | " | " | |
| 19 | $OCH_3$ | " | " | N | " | " | |
| 20 | " | " | O | " | " | " | |
| 21 | " | " | " | CH | cyclopentyl | " | 56–57 |
| 22 | Cl | " | " | " | " | " | |
| 23 | $CH_3$ | " | " | " | " | " | |
| 24 | $NHCH_3$ | " | " | " | " | " | |
| 25 | $OCH_3$ | " | S | " | " | " | |
| 26 | Cl | " | " | " | " | " | |
| 27 | $CH_3$ | " | " | " | " | " | |
| 28 | $NHCH_3$ | " | " | " | " | " | |

TABLE I-continued

| # | | | | | | | |
|---|---|---|---|---|---|---|---|
| 29 | $OCH_3$ | " | " | N | " | " | |
| 30 | " | " | O | " | " | " | |
| 31 | $OCH_3$ | $OCH_3$ | O | CH | $i\text{-}C_3H_7$ | $OCH_2COOCH_2C\equiv CH$ | 98 |
| 32 | Cl | " | " | " | " | " | |
| 33 | $CH_3$ | " | " | " | " | " | |
| 34 | $NHCH_3$ | " | " | " | " | " | |
| 35 | $OCH_3$ | " | S | " | " | " | |
| 36 | Cl | " | " | " | " | " | |
| 37 | $CH_3$ | " | " | " | " | " | |
| 38 | $NHCH_3$ | " | " | " | " | " | |
| 39 | $OCH_3$ | " | " | N | " | " | |
| 40 | " | " | O | " | " | " | |
| 41 | " | " | " | " | $t\text{-}C_4H_9$ | " | |
| 42 | Cl | " | " | " | " | " | |
| 43 | $CH_3$ | " | " | " | " | " | |
| 44 | $NHCH_3$ | " | " | " | " | " | |
| 45 | $OCH_3$ | " | " | " | " | " | |
| 46 | Cl | " | " | " | " | " | |
| 47 | $CH_3$ | " | " | " | " | " | |
| 48 | $NHCH_3$ | " | " | " | " | " | |
| 49 | $OCH_3$ | " | " | N | " | " | |
| 50 | " | " | O | " | " | " | |
| 51 | " | " | " | CH | cyclopentyl | " | 81–82 |
| 52 | Cl | " | " | " | " | " | |
| 53 | $CH_3$ | " | " | " | " | " | |
| 54 | $NHCH_3$ | " | " | " | " | " | |
| 55 | $OCH_3$ | " | S | " | " | " | |
| 56 | Cl | " | " | " | " | " | |
| 57 | $CH_3$ | " | " | " | " | " | |
| 58 | $NHCH_3$ | " | " | " | " | " | |
| 59 | $OCH_3$ | " | " | N | " | " | |
| 60 | " | " | O | " | " | " | |
| 61 | $OCH_3$ | $OCH_3$ | O | CH | $i\text{-}C_3H_7$ | $OCH_2COOCH_2Ph$ | oil |
| 62 | Cl | " | " | " | " | " | |
| 63 | $CH_3$ | " | " | " | " | " | |
| 64 | $NHCH_3$ | " | " | " | " | " | |
| 65 | $OCH_3$ | " | S | " | " | " | |
| 66 | Cl | " | " | " | " | " | |
| 67 | $CH_3$ | " | " | " | " | " | |
| 68 | $NHCH_3$ | " | " | " | " | " | |
| 69 | $OCH_3$ | " | " | N | " | " | |
| 70 | " | " | O | " | " | " | |
| 71 | " | " | " | " | t-Bu | " | |
| 72 | Cl | " | " | " | " | " | |
| 73 | $CH_3$ | " | " | " | " | " | |
| 74 | $NHCH_3$ | " | " | " | " | " | |
| 75 | $OCH_3$ | " | " | " | " | " | |
| 76 | Cl | " | " | " | " | " | |
| 77 | $CH_3$ | " | " | " | " | " | |
| 78 | $NHCH_3$ | " | " | " | " | " | |
| 79 | $OCH_3$ | " | " | N | " | " | |
| 80 | " | " | O | " | " | " | |
| 81 | " | " | " | CH | cyclopentyl | " | 66–68 |
| 82 | Cl | " | " | " | " | " | |
| 83 | $CH_3$ | " | " | " | " | " | |
| 84 | $NHCH_3$ | " | " | " | " | " | |
| 85 | $OCH_3$ | " | S | " | " | " | |
| 86 | Cl | " | " | " | " | " | |
| 87 | $CH_3$ | " | " | " | " | " | |
| 88 | $NHCH_3$ | " | " | " | " | " | |
| 89 | $OCH_3$ | " | " | N | " | " | |
| 90 | " | " | O | " | " | " | |
| 91 | $OCH_3$ | $OCH_3$ | O | CH | $i\text{-}C_3H_7$ | $OCH_2COSCH_3$ | |
| 92 | Cl | " | " | " | " | " | |
| 93 | $CH_3$ | " | " | " | " | " | |
| 94 | $NHCH_3$ | " | " | " | " | " | |
| 95 | $OCH_3$ | " | S | " | " | " | |
| 96 | Cl | " | " | " | " | " | |
| 97 | $CH_3$ | " | " | " | " | " | |
| 98 | $NHCH_3$ | " | " | " | " | " | |
| 99 | $OCH_3$ | " | " | N | " | " | |
| 100 | " | " | O | " | " | " | |
| 101 | " | " | " | " | t-Bu | " | |
| 102 | Cl | " | " | " | " | " | |
| 103 | $CH_3$ | " | " | " | " | " | |
| 104 | $NHCH_3$ | " | " | " | " | " | |
| 105 | $OCH_3$ | " | " | " | " | " | |
| 106 | Cl | " | " | " | " | " | |
| 107 | $CH_3$ | " | " | " | " | " | |
| 108 | $NHCH_3$ | " | " | " | " | " | |
| 109 | $OCH_3$ | " | " | N | " | " | |
| 110 | " | " | O | " | " | " | |

TABLE I-continued

| No. | | | | | | |
|---|---|---|---|---|---|---|
| 111 | " | " | " | CH | cyclopentyl | " |
| 112 | Cl | " | " | " | " | " |
| 113 | CH₃ | " | " | " | " | " |
| 114 | NHCH₃ | " | " | " | " | " |
| 115 | OCH₃ | " | S | " | " | " |
| 116 | Cl | " | " | " | " | " |
| 117 | CH₃ | " | " | " | " | " |
| 118 | NHCH₃ | " | " | " | " | " |
| 119 | OCH₃ | " | " | N | " | " |
| 120 | " | " | O | " | " | " |
| 121 | OCH₃ | OCH₃ | O | CH | i-C₃H₇ | OCH₂COSC₂H₅ |
| 122 | Cl | " | " | " | " | " |
| 123 | CH₃ | " | " | " | " | " |
| 124 | NHCH₃ | " | " | " | " | " |
| 125 | OCH₃ | " | S | " | " | " |
| 126 | Cl | " | " | " | " | " |
| 127 | CH₃ | " | " | " | " | " |
| 128 | NHCH₃ | " | " | " | " | " |
| 129 | OCH₃ | " | " | N | " | " |
| 130 | " | " | O | " | " | " |
| 131 | " | " | " | " | t-Bu | " |
| 132 | Cl | " | " | " | " | " |
| 133 | CH₃ | " | " | " | " | " |
| 134 | NHCH₃ | " | " | " | " | " |
| 135 | OCH₃ | " | " | " | " | " |
| 136 | Cl | " | " | " | " | " |
| 137 | CH₃ | " | " | " | " | " |
| 138 | NHCH₃ | " | " | " | " | " |
| 139 | OCH₃ | " | " | N | " | " |
| 140 | " | " | O | " | " | " |
| 141 | " | " | " | CH | cyclopentyl | " |
| 142 | Cl | " | " | " | " | " |
| 143 | CH₃ | " | " | " | " | " |
| 144 | NHCH₃ | " | " | " | " | " |
| 145 | OCH₃ | " | S | " | " | " |
| 146 | Cl | " | " | " | " | " |
| 147 | CH₃ | " | " | " | " | " |
| 148 | NHCH₃ | " | " | " | " | " |
| 149 | OCH₃ | " | " | N | " | " |
| 150 | " | " | O | " | " | " |
| 151 | OCH₃ | OCH₃ | O | CH | i-C₃H₇ | OCH₂COSCH₂Ph |
| 152 | Cl | " | " | " | " | " |
| 153 | CH₃ | " | " | " | " | " |
| 154 | NHCH₃ | " | " | " | " | " |
| 155 | OCH₃ | " | S | " | " | " |
| 156 | Cl | " | " | " | " | " |
| 157 | CH₃ | " | " | " | " | " |
| 158 | NHCH₃ | " | " | " | " | " |
| 159 | OCH₃ | " | " | N | " | " |
| 160 | " | " | O | " | " | " |
| 161 | " | " | " | " | t-Bu | " |
| 162 | Cl | " | " | " | " | " |
| 163 | CH₃ | " | " | " | " | " |
| 164 | NHCH₃ | " | " | " | " | " |
| 165 | OCH₃ | " | " | " | " | " |
| 166 | Cl | " | " | " | " | " |
| 167 | CH₃ | " | " | " | " | " |
| 168 | NHCH₃ | " | " | " | " | " |
| 169 | OCH₃ | " | " | N | " | " |
| 170 | " | " | O | " | " | " |
| 171 | " | " | " | CH | cyclopentyl | " |
| 172 | Cl | " | " | " | " | " |
| 173 | CH₃ | " | " | " | " | " |
| 174 | NHCH₃ | " | " | " | " | " |
| 175 | OCH₃ | " | S | " | " | " |
| 176 | Cl | " | " | " | " | " |
| 177 | CH₃ | " | " | " | " | " |
| 178 | NHCH₃ | " | " | " | " | " |
| 179 | OCH₃ | " | " | N | " | " |
| 180 | " | " | O | " | " | " |
| 181 | OCH₃ | OCH₃ | O | CH | i-C₃H₇ | OCH(CH₃)COOCH₂CH=CH₂ |
| 182 | Cl | " | " | " | " | " |
| 183 | CH₃ | " | " | " | " | " |
| 184 | NHCH₃ | " | " | " | " | " |
| 185 | OCH₃ | " | S | " | " | " |
| 186 | Cl | " | " | " | " | " |
| 187 | CH₃ | " | " | " | " | " |
| 188 | NHCH₃ | " | " | " | " | " |
| 189 | OCH₃ | " | " | N | " | " |
| 190 | " | " | O | " | " | " |
| 191 | " | " | " | " | t-C₄H₉ | " |
| 192 | Cl | " | " | " | " | " |

TABLE I-continued

| | | | | | | |
|---|---|---|---|---|---|---|
| 193 CH₃ | " | " | " | " | " | |
| 194 NHCH₃ | " | " | " | " | " | |
| 195 OCH₃ | " | " | " | " | " | |
| 196 Cl | " | " | " | " | " | |
| 197 CH₃ | " | " | " | " | " | |
| 198 NHCH₃ | " | " | " | " | " | |
| 199 OCH₃ | " | " | N | " | " | |
| 200 " | " | O | " | " | " | |
| 201 " | " | " | CH | cyclopentyl | " | 62–64 |
| 202 Cl | " | " | " | " | " | |
| 203 CH₃ | " | " | " | " | " | |
| 204 NHCH₃ | " | " | " | " | " | |
| 205 OCH₃ | " | S | " | " | " | |
| 206 Cl | " | " | " | " | " | |
| 207 CH₃ | " | " | " | " | " | |
| 208 NHCH₃ | " | " | " | " | " | |
| 209 OCH₃ | " | " | N | " | " | |
| 210 " | " | O | " | " | " | |
| 211 OCH₃ | OCH₃ | O | CH | i-C₃H₇ | OCH(CH₃)COOCH₂C≡CH | 85 |
| 212 Cl | " | " | " | " | " | |
| 213 CH₃ | " | " | " | " | " | |
| 214 NHCH₃ | " | " | " | " | " | |
| 215 OCH₃ | " | S | " | " | " | |
| 216 Cl | " | " | " | " | " | |
| 217 CH₃ | " | " | " | " | " | |
| 218 NHCH₃ | " | " | " | " | " | |
| 219 OCH₃ | " | " | N | " | " | |
| 220 " | " | O | " | " | " | |
| 221 " | " | " | " | t-Bu | " | |
| 222 Cl | " | " | " | " | " | |
| 223 CH₃ | " | " | " | " | " | |
| 224 NHCH₃ | " | " | " | " | " | |
| 225 OCH₃ | " | " | " | " | " | |
| 226 Cl | " | " | " | " | " | |
| 227 CH₃ | " | " | " | " | " | |
| 228 NHCH₃ | " | " | " | " | " | |
| 229 OCH₃ | " | " | N | " | " | |
| 230 " | " | O | " | " | " | |
| 231 " | " | " | CH | cyclopentyl | " | oil |
| 232 Cl | " | " | " | " | " | |
| 233 CH₃ | " | " | " | " | " | |
| 234 NHCH₃ | " | " | " | " | " | |
| 235 OCH₃ | " | S | " | " | " | |
| 236 Cl | " | " | " | " | " | |
| 237 CH₃ | " | " | " | " | " | |
| 238 NHCH₃ | " | " | " | " | " | |
| 239 OCH₃ | " | " | N | " | " | |
| 240 " | " | O | " | " | " | |
| 241 OCH₃ | OCH₃ | O | CH | i-C₃H₇ | OCH(CH₃)COOCH₂Ph | |
| 242 Cl | " | " | " | " | " | |
| 243 CH₃ | " | " | " | " | " | |
| 244 NHCH₃ | " | " | " | " | " | |
| 245 OCH₃ | " | S | " | " | " | |
| 246 Cl | " | " | " | " | " | |
| 247 CH₃ | " | " | " | " | " | |
| 248 NHCH₃ | " | " | " | " | " | |
| 249 OCH₃ | " | " | N | " | " | |
| 250 " | " | O | " | " | " | |
| 251 " | " | " | " | t-Bu | " | |
| 252 Cl | " | " | " | " | " | |
| 253 CH₃ | " | " | " | " | " | |
| 254 NHCH₃ | " | " | " | " | " | |
| 255 OCH₃ | " | " | " | " | " | |
| 256 Cl | " | " | " | " | " | |
| 257 CH₃ | " | " | " | " | " | |
| 258 NHCH₃ | " | " | " | " | " | |
| 259 OCH₃ | " | " | N | " | " | |
| 260 " | " | O | " | " | " | |
| 261 " | " | " | CH | cyclopentyl | " | |
| 262 Cl | " | " | " | " | " | |
| 263 CH₃ | " | " | " | " | " | |
| 264 NHCH₃ | " | " | " | " | " | |
| 265 OCH₃ | " | S | " | " | " | |
| 266 Cl | " | " | " | " | " | |
| 267 CH₃ | " | " | " | " | " | |
| 268 NHCH₃ | " | " | " | " | " | |
| 269 OCH₃ | " | " | N | " | " | |
| 270 " | " | O | " | " | " | |
| 271 OCH₃ | OCH₃ | O | CH | i-C₃H₇ | OCH(CH₃)COSCH₃ | |
| 272 Cl | " | " | " | " | " | |
| 273 CH₃ | " | " | " | " | " | |
| 274 NHCH₃ | " | " | " | " | " | |

TABLE I-continued

| # | Col1 | Col2 | Col3 | Col4 | Col5 | Col6 |
|---|------|------|------|------|------|------|
| 275 | OCH₃ | " | S | " | " | " |
| 276 | Cl | " | " | " | " | " |
| 277 | CH₃ | " | " | " | " | " |
| 278 | NHCH₃ | " | " | " | " | " |
| 279 | OCH₃ | " | " | N | " | " |
| 280 | " | " | " | O | " | " |
| 281 | " | " | " | " | t-Bu | " |
| 282 | Cl | " | " | " | " | " |
| 283 | CH₃ | " | " | " | " | " |
| 284 | NHCH₃ | " | " | " | " | " |
| 285 | OCH₃ | " | " | " | " | " |
| 286 | Cl | " | " | " | " | " |
| 287 | CH₃ | " | " | " | " | " |
| 288 | NHCH₃ | " | " | " | " | " |
| 289 | OCH₃ | " | " | N | " | " |
| 290 | " | " | " | O | " | " |
| 291 | " | " | " | " | CH | cyclopentyl | " |
| 292 | Cl | " | " | " | " | " |
| 293 | CH₃ | " | " | " | " | " |
| 294 | NHCH₃ | " | " | " | " | " |
| 295 | OCH₃ | " | S | " | " | " |
| 296 | Cl | " | " | " | " | " |
| 297 | CH₃ | " | " | " | " | " |
| 298 | NHCH₃ | " | " | " | " | " |
| 299 | OCH₃ | " | " | N | " | " |
| 300 | " | " | " | O | " | " |
| 301 | OCH₃ | OCH₃ | O | CH | i-C₃H₇ | OCH(CH₃)COSC₂H₅ |
| 302 | Cl | " | " | " | " | " |
| 303 | CH₃ | " | " | " | " | " |
| 304 | NHCH₃ | " | " | " | " | " |
| 305 | OCH₃ | " | S | " | " | " |
| 306 | Cl | " | " | " | " | " |
| 307 | CH₃ | " | " | " | " | " |
| 308 | NHCH₃ | " | " | " | " | " |
| 309 | OCH₃ | " | " | N | " | " |
| 310 | " | " | " | O | " | " |
| 311 | " | " | " | " | t-Bu | " |
| 312 | Cl | " | " | " | " | " |
| 313 | CH₃ | " | " | " | " | " |
| 314 | NHCH₃ | " | " | " | " | " |
| 315 | OCH₃ | " | " | " | " | " |
| 316 | Cl | " | " | " | " | " |
| 317 | CH₃ | " | " | " | " | " |
| 318 | NHCH₃ | " | " | " | " | " |
| 319 | OCH₃ | " | " | N | " | " |
| 320 | " | " | " | O | " | " |
| 321 | " | " | " | " | CH | cyclopentyl | " |
| 322 | Cl | " | " | " | " | " |
| 323 | CH₃ | " | " | " | " | " |
| 324 | NHCH₃ | " | " | " | " | " |
| 325 | OCH₃ | " | S | " | " | " |
| 326 | Cl | " | " | " | " | " |
| 327 | CH₃ | " | " | " | " | " |
| 328 | NHCH₃ | " | " | " | " | " |
| 329 | OCH₃ | " | " | N | " | " |
| 330 | " | " | " | O | " | " |
| 331 | OCH₃ | OCH₃ | O | CH | i-C₃H₇ | OCH(CH₂)COSCH₂Ph |
| 332 | Cl | " | " | " | " | " |
| 333 | CH₃ | " | " | " | " | " |
| 334 | NHCH₃ | " | " | " | " | " |
| 335 | OCH₃ | " | S | " | " | " |
| 336 | Cl | " | " | " | " | " |
| 337 | CH₃ | " | " | " | " | " |
| 338 | NHCH₃ | " | " | " | " | " |
| 339 | OCH₃ | " | " | N | " | " |
| 340 | " | " | " | O | " | " |
| 341 | " | " | " | " | t-Bu | " |
| 342 | Cl | " | " | " | " | " |
| 343 | CH₃ | " | " | " | " | " |
| 344 | NHCH₃ | " | " | " | " | " |
| 345 | OCH₃ | " | " | " | " | " |
| 346 | Cl | " | " | " | " | " |
| 347 | CH₃ | " | " | " | " | " |
| 348 | NHCH₃ | " | " | " | " | " |
| 349 | OCH₃ | " | " | N | " | " |
| 350 | " | " | " | O | " | " |
| 351 | " | " | " | " | CH | cyclopentyl | " |
| 352 | Cl | " | " | " | " | " |
| 353 | CH₃ | " | " | " | " | " |
| 354 | NHCH₃ | " | " | " | " | " |
| 355 | OCH₃ | " | S | " | " | " |
| 356 | Cl | " | " | " | " | " |

TABLE I-continued

| # | R1 | R2 | X | Y | R3 | R4 | Note |
|---|----|----|---|---|----|----|------|
| 357 | CH₃ | " | " | " | " | " | |
| 358 | NHCH₃ | " | " | N | " | " | |
| 359 | OCH₃ | " | " | " | " | " | |
| 360 | " | " | O | " | " | " | |
| 361 | OCH₃ | OCH₃ | O | CH | i-C₃H₇ | —O—CH—C=O / CH₂CH₂—O | 131 |
| 362 | Cl | " | " | " | " | " | |
| 363 | CH₃ | " | " | " | " | " | |
| 364 | NHCH₃ | " | " | " | " | " | |
| 365 | OCH₃ | " | S | " | " | " | |
| 366 | Cl | " | " | " | " | " | |
| 367 | CH₃ | " | " | " | " | " | |
| 368 | NHCH₃ | " | " | " | " | " | |
| 369 | OCH₃ | " | " | N | " | " | |
| 370 | " | " | O | " | " | " | |
| 371 | " | " | " | " | t-Bu | " | |
| 372 | Cl | " | " | " | " | " | |
| 373 | CH₃ | " | " | " | " | " | |
| 374 | NHCH₃ | " | " | " | " | " | |
| 375 | OCH₃ | " | " | " | " | " | |
| 376 | Cl | " | " | " | " | " | |
| 377 | CH₃ | " | " | " | " | " | |
| 378 | NHCH₃ | " | " | " | " | " | |
| 379 | OCH₃ | " | " | N | " | " | |
| 380 | " | " | O | " | " | " | |
| 381 | " | " | " | CH | cyclopentyl | " | |
| 382 | Cl | " | " | " | " | " | |
| 383 | CH₃ | " | " | " | " | " | |
| 384 | NHCH₃ | " | " | " | " | " | |
| 385 | OCH₃ | " | S | " | " | " | |
| 386 | Cl | " | " | " | " | " | |
| 387 | CH₃ | " | " | " | " | " | |
| 388 | NHCH₃ | " | " | " | " | " | |
| 389 | OCH₃ | " | " | N | " | " | |
| 390 | " | " | O | " | " | " | |
| 391 | OCH₃ | OCH₃ | O | CH | i-C₃H₇ | OCH₂Si(CH₃)₃ | oil |
| 392 | Cl | " | " | " | " | " | |
| 393 | CH₃ | " | " | " | " | " | |
| 394 | NHCH₃ | " | " | " | " | " | |
| 395 | OCH₃ | " | S | " | " | " | |
| 396 | Cl | " | " | " | " | " | |
| 397 | CH₃ | " | " | " | " | " | |
| 398 | NHCH₃ | " | " | " | " | " | |
| 399 | OCH₃ | " | " | N | " | " | |
| 400 | " | " | O | " | " | " | |
| 401 | " | " | " | " | t-Bu | " | |
| 402 | Cl | " | " | " | " | " | |
| 403 | CH₃ | " | " | " | " | " | |
| 404 | NHCH₃ | " | " | " | " | " | |
| 405 | OCH₃ | " | " | " | " | " | |
| 406 | Cl | " | " | " | " | " | |
| 407 | CH₃ | " | " | " | " | " | |
| 408 | NHCH₃ | " | " | " | " | " | |
| 409 | OCH₃ | " | " | N | " | " | |
| 410 | " | " | O | " | " | " | " |
| 411 | " | " | " | CH | cyclopentyl | " | |
| 412 | Cl | " | " | " | " | " | |
| 413 | CH₃ | " | " | " | " | " | |
| 414 | NHCH₃ | " | " | " | " | " | |
| 415 | OCH₃ | " | S | " | " | " | |
| 416 | Cl | " | " | " | " | " | |
| 417 | CH₃ | " | " | " | " | " | |
| 418 | NHCH₃ | " | " | " | " | " | |
| 419 | OCH₃ | " | " | N | " | " | |
| 420 | " | " | O | " | " | " | " |
| 421 | OCH₃ | OCH₃ | O | CH | i-C₃H₇ | pyrid-2-ylmethoxy | |
| 422 | Cl | " | " | " | " | " | |
| 423 | CH₃ | " | " | " | " | " | |
| 424 | NHCH₃ | " | " | " | " | " | |
| 425 | OCH₃ | " | S | " | " | " | |
| 426 | Cl | " | " | " | " | " | |
| 427 | CH₃ | " | " | " | " | " | |
| 428 | NHCH₃ | " | " | " | " | " | |
| 429 | OCH₃ | " | " | N | " | " | |
| 430 | " | " | O | " | " | " | |
| 431 | " | " | " | " | t-Bu | " | |
| 432 | Cl | " | " | " | " | " | |
| 433 | CH₃ | " | " | " | " | " | |
| 434 | NHCH₃ | " | " | " | " | " | |

TABLE I-continued

| | | | | | | |
|---|---|---|---|---|---|---|
| 435 OCH₃ | " | " | " | " | " | |
| 436 Cl | " | " | " | " | " | |
| 437 CH₃ | " | " | " | " | " | |
| 438 NHCH₃ | " | " | " | " | " | |
| 439 OCH₃ | " | " | N | " | " | |
| 440 " | " | O | " | " | " | |
| 441 " | " | " | CH | cyclopentyl | " | 88–90 |
| 442 Cl | " | " | " | " | " | |
| 443 CH₃ | " | " | " | " | " | |
| 444 NHCH₃ | " | " | " | " | " | |
| 445 OCH₃ | " | S | " | " | " | |
| 446 Cl | " | " | " | " | " | |
| 447 CH₃ | " | " | " | " | " | |
| 448 NHCH₃ | " | " | " | " | " | |
| 449 OCH₃ | " | " | N | " | " | |
| 450 " | " | O | " | " | " | |
| 451 OCH₃ | OCH₃ | O | CH | i-C₃H₇ | pyrid-3-ylmethoxy | |
| 452 Cl | " | " | " | " | " | |
| 453 CH₃ | " | " | " | " | " | |
| 454 NHCH₃ | " | " | " | " | " | |
| 455 OCH₃ | " | S | " | " | " | |
| 456 Cl | " | " | " | " | " | |
| 457 CH₃ | " | " | " | " | " | |
| 458 NHCH₃ | " | " | " | " | " | |
| 459 OCH₃ | " | " | N | " | " | |
| 460 " | " | O | " | " | " | |
| 461 " | " | " | " | t-Bu | " | |
| 462 Cl | " | " | " | " | " | |
| 463 CH₃ | " | " | " | " | " | |
| 464 NHCH₃ | " | " | " | " | " | |
| 465 OCH₃ | " | " | " | " | " | |
| 466 Cl | " | " | " | " | " | |
| 467 CH₃ | " | " | " | " | " | |
| 468 NHCH₃ | " | " | " | " | " | |
| 469 OCH₃ | " | " | N | " | " | |
| 470 " | " | O | " | " | " | |
| 471 " | " | " | CH | cyclopentyl | " | |
| 472 Cl | " | " | " | " | " | |
| 473 CH₃ | " | " | " | " | " | |
| 474 NHCH₃ | " | " | " | " | " | |
| 475 OCH₃ | " | S | " | " | " | |
| 476 Cl | " | " | " | " | " | |
| 477 CH₃ | " | " | " | " | " | |
| 478 NHCH₃ | " | " | " | " | " | |
| 479 OCH₃ | " | " | N | " | " | |
| 480 " | " | O | " | " | " | |
| 481 OCH₃ | OCH₃ | O | CH | i-C₃H₇ | O—CH₂—P(=O)(CH₃)₂ | |
| 482 Cl | " | " | " | " | " | |
| 483 CH₃ | " | " | " | " | " | |
| 484 NHCH₃ | " | " | " | " | " | |
| 485 OCH₃ | " | S | " | " | " | |
| 486 Cl | " | " | " | " | " | |
| 487 CH₃ | " | " | " | " | " | |
| 488 NHCH₃ | " | " | " | " | " | |
| 489 OCH₃ | " | " | N | " | " | |
| 490 " | " | O | " | " | " | |
| 491 " | " | " | " | t-Bu | " | |
| 492 Cl | " | " | " | " | " | |
| 493 CH₃ | " | " | " | " | " | |
| 494 NHCH₃ | " | " | " | " | " | |
| 495 OCH₃ | " | " | " | " | " | |
| 496 Cl | " | " | " | " | " | |
| 497 CH₃ | " | " | " | " | " | |
| 498 NHCH₃ | " | " | " | " | " | |
| 499 OCH₃ | " | " | N | " | " | |
| 500 " | " | O | " | " | " | |
| 501 " | " | " | CH | cyclopentyl | " | oil |
| 502 Cl | " | " | " | " | " | |
| 503 CH₃ | " | " | " | " | " | |
| 504 NHCH₃ | " | " | " | " | " | |
| 505 OCH₃ | " | S | " | " | " | |
| 506 Cl | " | " | " | " | " | |
| 507 CH₃ | " | " | " | " | " | |
| 508 NHCH₃ | " | " | " | " | " | |
| 509 OCH₃ | " | " | N | " | " | |
| 510 " | " | O | " | " | " | |
| 511 OCH₃ | OCH₃ | O | CH | i-C₃H₇ | O—Si(CH₃)₂(t-Bu) | oil |
| 512 Cl | " | " | " | " | " | |
| 513 CH₃ | " | " | " | " | " | |
| 514 NHCH₃ | " | " | " | " | " | |
| 515 OCH₃ | " | S | " | " | " | |
| 516 Cl | " | " | " | " | " | |

TABLE I-continued

| No. | | | | | | | |
|---|---|---|---|---|---|---|---|
| 517 | CH₃ | " | " | " | " | " | |
| 518 | NHCH₃ | " | " | " | " | " | |
| 519 | OCH₃ | " | " | N | " | " | |
| 520 | " | " | O | " | " | " | |
| 521 | " | " | " | " | t-Bu | " | |
| 522 | Cl | " | " | " | " | " | |
| 523 | CH₃ | " | " | " | " | " | |
| 524 | NHCH₃ | " | " | " | " | " | |
| 525 | OCH₃ | " | " | " | " | " | |
| 526 | Cl | " | " | " | " | " | |
| 527 | CH₃ | " | " | " | " | " | |
| 528 | NHCH₃ | " | " | " | " | " | |
| 529 | OCH₃ | " | " | N | " | " | |
| 530 | " | " | O | " | " | " | |
| 531 | " | " | " | CH | cyclopentyl | " | |
| 532 | Cl | " | " | " | " | " | |
| 533 | CH₃ | " | " | " | " | " | |
| 534 | NHCH₃ | " | " | " | " | " | |
| 535 | OCH₃ | " | S | " | " | " | |
| 536 | Cl | " | " | " | " | " | |
| 537 | CH₃ | " | " | " | " | " | |
| 538 | NHCH₃ | " | " | " | " | " | |
| 539 | OCH₃ | " | " | N | " | " | |
| 540 | " | " | O | " | " | " | |
| 541 | OCH₃ | OCH₃ | O | CH | i-C₃H₇ | O—Si(i-Pr)₃ | 1.4800 |
| 542 | Cl | " | " | " | " | " | |
| 543 | CH₃ | " | " | " | " | " | |
| 544 | NHCH₃ | " | " | " | " | " | |
| 545 | OCH₃ | " | S | " | " | " | |
| 546 | Cl | " | " | " | " | " | |
| 547 | CH₃ | " | " | " | " | " | |
| 548 | NHCH₃ | " | " | " | " | " | |
| 549 | OCH₃ | " | " | N | " | " | |
| 550 | " | " | O | " | " | " | |
| 551 | " | " | " | " | t-Bu | " | |
| 552 | Cl | " | " | " | " | " | |
| 553 | CH₃ | " | " | " | " | " | |
| 554 | NHCH₃ | " | " | " | " | " | |
| 555 | OCH₃ | " | " | " | " | " | |
| 556 | Cl | " | " | " | " | " | |
| 557 | CH₃ | " | " | " | " | " | |
| 558 | NHCH₃ | " | " | " | " | " | |
| 559 | OCH₃ | " | " | N | " | " | |
| 560 | " | " | O | " | " | " | |
| 561 | " | " | " | CH | cyclopentyl | " | |
| 562 | Cl | " | " | " | " | " | |
| 563 | CH₃ | " | " | " | " | " | |
| 564 | NHCH₃ | " | " | " | " | " | |
| 565 | OCH₃ | " | S | " | " | " | |
| 566 | Cl | " | " | " | " | " | |
| 567 | CH₃ | " | " | " | " | " | |
| 568 | NHCH₃ | " | " | " | " | " | |
| 569 | OCH₃ | " | " | N | " | " | |
| 570 | " | " | O | " | " | " | |
| 571 | OCH₃ | OCH₃ | O | CH | i-C₃H₇ | —OCH₂C(OCH₃)=CHCOOCH₃ | 77–78 |
| 572 | Cl | " | " | " | " | " | |
| 573 | CH₃ | " | " | " | " | " | |
| 574 | NHCH₃ | " | " | " | " | " | |
| 575 | OCH₃ | " | S | " | " | " | |
| 576 | Cl | " | " | " | " | " | |
| 577 | CH₃ | " | " | " | " | " | |
| 578 | NHCH₃ | " | " | " | " | " | |
| 579 | OCH₃ | " | " | N | " | " | |
| 580 | " | " | O | " | " | " | |
| 581 | " | " | " | " | t-Bu | " | |
| 582 | Cl | " | " | " | " | " | |
| 583 | CH₃ | " | " | " | " | " | |
| 584 | NHCH₃ | " | " | " | " | " | |
| 585 | OCH₃ | " | " | " | " | " | |
| 586 | Cl | " | " | " | " | " | |
| 587 | CH₃ | " | " | " | " | " | |
| 588 | NHCH₃ | " | " | " | " | " | |
| 589 | OCH₃ | " | " | N | " | " | |
| 590 | " | " | O | " | " | " | |
| 591 | " | " | " | CH | cyclopentyl | " | 72–74 |
| 592 | Cl | " | " | " | " | " | |
| 593 | CH₃ | " | " | " | " | " | |
| 594 | NHCH₃ | " | " | " | " | " | |
| 595 | OCH₃ | " | S | " | " | " | |
| 596 | Cl | " | " | " | " | " | |
| 597 | CH₃ | " | " | " | " | " | |
| 598 | NHCH₃ | " | " | " | " | " | |

TABLE I-continued

| | | | | | | |
|---|---|---|---|---|---|---|
| 599 | OCH₃ | " | N | " | " | |
| 600 | " | " | O | " | " | |
| 601 | OCH₃ | OCH₃ | O | CH | i-C₃H₇ | O—CH₂COOCH₂COOCH₃ | oil |
| 602 | Cl | " | " | " | " | " | |
| 603 | CH₃ | " | " | " | " | " | |
| 604 | NHCH₃ | " | " | " | " | " | |
| 605 | OCH₃ | " | S | " | " | " | |
| 606 | Cl | " | " | " | " | " | |
| 607 | CH₃ | " | " | " | " | " | |
| 608 | NHCH₃ | " | " | " | " | " | |
| 609 | OCH₃ | " | " | N | " | " | |
| 610 | " | " | O | " | " | " | |
| 611 | " | " | " | " | t-Bu | " | |
| 612 | Cl | " | " | " | " | " | |
| 613 | CH₃ | " | " | " | " | " | |
| 614 | NHCH₃ | " | " | " | " | " | |
| 615 | OCH₃ | " | " | " | " | " | |
| 616 | Cl | " | " | " | " | " | |
| 617 | CH₃ | " | " | " | " | " | |
| 618 | NHCH₃ | " | " | " | " | " | |
| 619 | OCH₃ | " | " | N | " | " | |
| 620 | " | " | O | " | " | " | |
| 621 | " | " | " | CH | cyclopentyl | " | 72–74 |
| 622 | Cl | " | " | " | " | " | |
| 623 | CH₃ | " | " | " | " | " | |
| 624 | NHCH₃ | " | " | " | " | " | |
| 625 | OCH₃ | " | S | " | " | " | |
| 626 | Cl | " | " | " | " | " | |
| 627 | CH₃ | " | " | " | " | " | |
| 628 | NHCH₃ | " | " | " | " | " | |
| 629 | OCH₃ | " | " | N | " | " | |
| 630 | " | " | O | " | " | " | |
| 631 | OCH₃ | OCH₃ | O | CH | i-C₃H₇ | OCH₂SO₂CH₃ | 108–110 |
| 632 | Cl | " | " | " | " | " | |
| 633 | CH₃ | " | " | " | " | " | |
| 634 | NHCH₃ | " | " | " | " | " | |
| 635 | OCH₃ | " | S | " | " | " | |
| 636 | Cl | " | " | " | " | " | |
| 637 | CH₃ | " | " | " | " | " | |
| 638 | NHCH₃ | " | " | " | " | " | |
| 639 | OCH₃ | " | " | N | " | " | |
| 640 | " | " | O | " | " | " | |
| 641 | " | " | " | " | t-Bu | " | |
| 642 | Cl | " | " | " | " | " | |
| 643 | CH₃ | " | " | " | " | " | |
| 644 | NHCH₃ | " | " | " | " | " | |
| 645 | OCH₃ | " | " | " | " | " | |
| 646 | Cl | " | " | " | " | " | |
| 647 | CH₃ | " | " | " | " | " | |
| 648 | NHCH₃ | " | " | " | " | " | |
| 649 | OCH₃ | " | " | N | " | " | |
| 650 | " | " | O | " | " | " | |
| 651 | " | " | " | CH | cyclopentyl | " | |
| 652 | Cl | " | " | " | " | " | |
| 653 | CH₃ | " | " | " | " | " | |
| 654 | NHCH₃ | " | " | " | " | " | |
| 655 | OCH₃ | " | S | " | " | " | |
| 656 | Cl | " | " | " | " | " | |
| 657 | CH₃ | " | " | " | " | " | |
| 658 | NHCH₃ | " | " | " | " | " | |
| 659 | OCH₃ | " | " | N | " | " | |
| 660 | " | " | O | " | " | " | |
| 661 | OCH₃ | OCH₃ | O | CH | i-C₃H₇ | OCH₂S(O)CH₂CH₃ | |
| 662 | Cl | " | " | " | " | " | |
| 663 | CH₃ | " | " | " | " | " | |
| 664 | NHCH₃ | " | " | " | " | " | |
| 665 | OCH₃ | " | S | " | " | " | |
| 666 | Cl | " | " | " | " | " | |
| 667 | CH₃ | " | " | " | " | " | |
| 668 | NHCH₃ | " | " | " | " | " | |
| 669 | OCH₃ | " | " | N | " | " | |
| 670 | " | " | O | " | " | " | |
| 671 | " | " | " | " | t-Bu | " | |
| 672 | Cl | " | " | " | " | " | |
| 673 | CH₃ | " | " | " | " | " | |
| 674 | NHCH₃ | " | " | " | " | " | |
| 675 | OCH₃ | " | S | " | " | " | |
| 676 | Cl | " | " | " | " | " | |
| 677 | CH₃ | " | " | " | " | " | |
| 678 | NHCH₃ | " | " | " | " | " | |
| 679 | OCH₃ | " | " | N | " | " | |
| 680 | " | " | O | " | " | " | |

TABLE I-continued

| | | | | | | |
|---|---|---|---|---|---|---|
| 681 | " | " | " | CH | cyclopentyl | " |
| 682 | Cl | " | " | " | " | " |
| 683 | CH₃ | " | " | " | " | " |
| 684 | NHCH₃ | " | " | " | " | " |
| 685 | OCH₃ | " | S | " | " | " |
| 686 | Cl | " | " | " | " | " |
| 687 | CH₃ | " | " | " | " | " |
| 688 | NHCH₃ | " | " | " | " | " |
| 689 | OCH₃ | " | " | N | " | " |
| 690 | " | " | O | " | " | " |
| 691 | OCH₃ | OCH₃ | O | CH | i-C₃H₇ | OCH₂SOCH₃ | 76–78 |
| 692 | Cl | " | " | " | " | " |
| 693 | CH₃ | " | " | " | " | " |
| 694 | NHCH₃ | " | " | " | " | " |
| 695 | OCH₃ | " | S | " | " | " |
| 696 | Cl | " | " | " | " | " |
| 697 | CH₃ | " | " | " | " | " |
| 698 | NHCH₃ | " | " | " | " | " |
| 699 | OCH₃ | " | " | N | " | " |
| 700 | " | " | O | " | " | " |
| 701 | " | " | " | " | t-Bu | " |
| 702 | Cl | " | " | " | " | " |
| 703 | CH₃ | " | " | " | " | " |
| 704 | NHCH₃ | " | " | " | " | " |
| 705 | OCH₃ | " | " | " | " | " |
| 706 | Cl | " | " | " | " | " |
| 707 | CH₃ | " | " | " | " | " |
| 708 | NHCH₃ | " | " | " | " | " |
| 709 | OCH₃ | " | " | N | " | " |
| 710 | " | " | O | " | " | " |
| 711 | " | " | " | CH | cyclopentyl | " |
| 712 | Cl | " | " | " | " | " |
| 713 | CH₃ | " | " | " | " | " |
| 714 | NHCH₃ | " | " | " | " | " |
| 715 | OCH₃ | " | S | " | " | " |
| 716 | Cl | " | " | " | " | " |
| 717 | CH₃ | " | " | " | " | " |
| 718 | NHCH₃ | " | " | " | " | " |
| 719 | OCH₃ | " | " | N | " | " |
| 720 | " | " | O | " | " | " |
| 721 | OCH₃ | OCH₃ | O | CH | i-C₃H₇ | OCH₂SO₂C₂H₅ |
| 722 | Cl | " | " | " | " | " |
| 723 | CH₃ | " | " | " | " | " |
| 724 | NHCH₃ | " | " | " | " | " |
| 725 | OCH₃ | " | S | " | " | " |
| 726 | Cl | " | " | " | " | " |
| 727 | CH₃ | " | " | " | " | " |
| 728 | NHCH₃ | " | " | " | " | " |
| 729 | OCH₃ | " | " | N | " | " |
| 730 | " | " | O | " | " | " |
| 731 | " | " | " | " | t-Bu | " |
| 732 | Cl | " | " | " | " | " |
| 733 | CH₃ | " | " | " | " | " |
| 734 | NHCH₃ | " | " | " | " | " |
| 735 | OCH₃ | " | " | " | " | " |
| 736 | Cl | " | " | " | " | " |
| 737 | CH₃ | " | " | " | " | " |
| 738 | NHCH₃ | " | " | " | " | " |
| 739 | OCH₃ | " | " | N | " | " |
| 740 | " | " | O | " | " | " |
| 741 | " | " | " | CH | cyclopentyl | " |
| 742 | Cl | " | " | " | " | " |
| 743 | CH₃ | " | " | " | " | " |
| 744 | NHCH₃ | " | " | " | " | " |
| 745 | OCH₃ | " | S | " | " | " |
| 746 | Cl | " | " | " | " | " |
| 747 | CH₃ | " | " | " | " | " |
| 748 | NHCH₃ | " | " | " | " | " |
| 749 | OCH₃ | " | " | N | " | " |
| 750 | " | " | O | " | " | " |
| 751 | OCH₃ | OCH₃ | O | CH | i-C₃H₇ | OCH₂CH₂SO₂C₂H₅ |
| 752 | Cl | " | " | " | " | " |
| 753 | CH₃ | " | " | " | " | " |
| 754 | NHCH₃ | " | " | " | " | " |
| 755 | OCH₃ | " | S | " | " | " |
| 756 | Cl | " | " | " | " | " |
| 757 | CH₃ | " | " | " | " | " |
| 758 | NHCH₃ | " | " | " | " | " |
| 759 | OCH₃ | " | " | N | " | " |
| 760 | " | " | O | " | " | " |
| 761 | " | " | " | " | t-Bu | " |
| 762 | Cl | " | " | " | " | " |

TABLE I-continued

| | | | | | |
|---|---|---|---|---|---|
| 763 | CH₃ | " | " | " | " | " |
| 764 | NHCH₃ | " | " | " | " | " |
| 765 | OCH₃ | " | " | " | " | " |
| 766 | Cl | " | " | " | " | " |
| 767 | CH₃ | " | " | " | " | " |
| 768 | NHCH₃ | " | " | " | " | " |
| 769 | OCH₃ | " | " | N | " | " |
| 770 | " | " | O | " | " | " |
| 771 | " | " | " | CH | cyclopentyl | " |
| 772 | Cl | " | " | " | " | " |
| 773 | CH₃ | " | " | " | " | " |
| 774 | NHCH₃ | " | " | " | " | " |
| 775 | OCH₃ | " | S | " | " | " |
| 776 | Cl | " | " | " | " | " |
| 777 | CH₃ | " | " | " | " | " |
| 778 | NHCH₃ | " | " | " | " | " |
| 779 | OCH₃ | " | " | N | " | " |
| 780 | " | " | O | " | " | " |
| 781 | OCH₃ | OCH₃ | O | CH | i-C₃H₇ | OC₃H₆OCH₂CH=CH₂ |
| 782 | Cl | " | " | " | " | " |
| 783 | CH₃ | " | " | " | " | " |
| 784 | NHCH₃ | " | " | " | " | " |
| 785 | OCH₃ | " | S | " | " | " |
| 786 | Cl | " | " | " | " | " |
| 787 | CH₃ | " | " | " | " | " |
| 788 | NHCH₃ | " | " | " | " | " |
| 789 | OCH₃ | " | " | N | " | " |
| 790 | " | " | O | " | " | " |
| 791 | " | " | " | " | t-Bu | " |
| 792 | Cl | " | " | " | " | " |
| 793 | CH₃ | " | " | " | " | " |
| 794 | NHCH₃ | " | " | " | " | " |
| 795 | OCH₃ | " | " | " | " | " |
| 796 | Cl | " | " | " | " | " |
| 797 | CH₃ | " | " | " | " | " |
| 798 | NHCH₃ | " | " | " | " | " |
| 799 | OCH₃ | " | " | N | " | " |
| 800 | " | " | O | " | " | " |
| 801 | " | " | " | CH | cyclopentyl | " |
| 802 | Cl | " | " | " | " | " |
| 803 | CH₃ | " | " | " | " | " |
| 804 | NHCH₃ | " | " | " | " | " |
| 805 | OCH₃ | " | S | " | " | " |
| 806 | Cl | " | " | " | " | " |
| 807 | CH₃ | " | " | " | " | " |
| 808 | NHCH₃ | " | " | " | " | " |
| 809 | OCH₃ | " | " | N | " | " |
| 810 | " | " | O | " | " | " |
| 811 | OCH₃ | OCH₃ | O | CH | i-C₃H₇ | OCH₂CH₂OCH₂Ph |
| 812 | Cl | " | " | " | " | " |
| 813 | CH₃ | " | " | " | " | " |
| 814 | NHCH₃ | " | " | " | " | " |
| 815 | OCH₃ | " | S | " | " | " |
| 816 | Cl | " | " | " | " | " |
| 817 | CH₃ | " | " | " | " | " |
| 818 | NHCH₃ | " | " | " | " | " |
| 819 | OCH₃ | " | " | N | " | " |
| 820 | " | " | O | " | " | " |
| 821 | " | " | " | " | t-Bu | " |
| 822 | Cl | " | " | " | " | " |
| 823 | CH₃ | " | " | " | " | " |
| 824 | NHCH₃ | " | " | " | " | " |
| 825 | OCH₃ | " | " | " | " | " |
| 826 | Cl | " | " | " | " | " |
| 827 | CH₃ | " | " | " | " | " |
| 828 | NHCH₃ | " | " | " | " | " |
| 829 | OCH₃ | " | " | N | " | " |
| 830 | " | " | O | " | " | " |
| 831 | " | " | " | CH | cyclopentyl | " |
| 832 | Cl | " | " | " | " | " |
| 833 | CH₃ | " | " | " | " | " |
| 834 | NHCH₃ | " | " | " | " | " |
| 835 | OCH₃ | " | S | " | " | " |
| 836 | Cl | " | " | " | " | " |
| 837 | CH₃ | " | " | " | " | " |
| 838 | NHCH₃ | " | " | " | " | " |
| 839 | OCH₃ | " | " | N | " | " |
| 840 | " | " | O | " | " | " |
| 841 | OCH₃ | OCH₃ | O | CH | i-C₃H₇ | OCH₂CH₂—O—CH₂C≡CH |
| 842 | Cl | " | " | " | " | " |
| 843 | CH₃ | " | " | " | " | " |
| 844 | NHCH₃ | " | " | " | " | " |

TABLE I-continued

| No. | | | | | | | |
|---|---|---|---|---|---|---|---|
| 845 | OCH₃ | " | S | " | " | " | |
| 846 | Cl | " | " | " | " | " | |
| 847 | CH₃ | " | " | " | " | " | |
| 848 | NHCH₃ | " | " | " | " | " | |
| 849 | OCH₃ | " | " | N | " | " | |
| 850 | " | " | " | O | " | " | |
| 851 | " | " | " | " | t-Bu | " | |
| 852 | Cl | " | " | " | " | " | |
| 853 | CH₃ | " | " | " | " | " | |
| 854 | NHCH₃ | " | " | " | " | " | |
| 855 | OCH₃ | " | " | " | " | " | |
| 856 | Cl | " | " | " | " | " | |
| 857 | CH₃ | " | " | " | " | " | |
| 858 | NHCH₃ | " | " | " | " | " | |
| 859 | OCH₃ | " | " | N | " | " | |
| 860 | " | " | " | O | " | " | |
| 861 | " | " | " | " | CH cyclopentyl | " | |
| 862 | Cl | " | " | " | " | " | |
| 863 | CH₃ | " | " | " | " | " | |
| 864 | NHCH₃ | " | " | " | " | " | |
| 865 | OCH₃ | " | " | S | " | " | |
| 866 | Cl | " | " | " | " | " | |
| 867 | CH₃ | " | " | " | " | " | |
| 868 | NHCH₃ | " | " | " | " | " | |
| 869 | OCH₃ | " | " | N | " | " | |
| 870 | " | " | " | O | " | " | |
| 871 | OCH₃ | OCH₃ | O | CH | i-C₃H₇ | —OCH₂CH(CH₃)OCH₂CH=CH₂ | oil |
| 872 | Cl | " | " | " | " | " | |
| 873 | CH₃ | " | " | " | " | " | |
| 874 | NHCH₃ | " | " | " | " | " | |
| 875 | OCH₃ | " | " | S | " | " | |
| 876 | Cl | " | " | " | " | " | |
| 877 | CH₃ | " | " | " | " | " | |
| 878 | NHCH₃ | " | " | " | " | " | |
| 879 | OCH₃ | " | " | N | " | " | |
| 880 | " | " | " | O | " | " | |
| 881 | " | " | " | " | t-Bu | " | |
| 882 | Cl | " | " | " | " | " | |
| 883 | CH₃ | " | " | " | " | " | |
| 884 | NHCH₃ | " | " | " | " | " | |
| 885 | OCH₃ | " | " | " | " | " | |
| 886 | Cl | " | " | " | " | " | |
| 887 | CH₃ | " | " | " | " | " | |
| 888 | NHCH₃ | " | " | " | " | " | |
| 889 | OCH₃ | " | " | N | " | " | |
| 890 | " | " | " | O | " | " | |
| 891 | " | " | " | " | CH cyclopentyl | " | oil |
| 892 | Cl | " | " | " | " | " | |
| 893 | CH₃ | " | " | " | " | " | |
| 894 | NHCH₃ | " | " | " | " | " | |
| 895 | OCH₃ | " | " | S | " | " | |
| 896 | Cl | " | " | " | " | " | |
| 897 | CH₃ | " | " | " | " | " | |
| 898 | NHCH₃ | " | " | " | " | " | |
| 899 | OCH₃ | " | " | N | " | " | |
| 900 | " | " | " | O | " | " | |
| 901 | OCH₃ | OCH₃ | O | CH | i-C₃H₇ | OC₄H₈—O—CH₂—CH=CH₂ | |
| 902 | Cl | " | " | " | " | " | |
| 903 | CH₃ | " | " | " | " | " | |
| 904 | NHCH₃ | " | " | " | " | " | |
| 905 | OCH₃ | " | " | S | " | " | |
| 906 | Cl | " | " | " | " | " | |
| 907 | CH₃ | " | " | " | " | " | |
| 908 | NHCH₃ | " | " | " | " | " | |
| 909 | OCH₃ | " | " | N | " | " | |
| 910 | " | " | " | O | " | " | |
| 911 | " | " | " | " | t-Bu | " | |
| 912 | Cl | " | " | " | " | " | |
| 913 | CH₃ | " | " | " | " | " | |
| 914 | NHCH₃ | " | " | " | " | " | |
| 915 | OCH₃ | " | " | " | " | " | |
| 916 | Cl | " | " | " | " | " | |
| 917 | CH₃ | " | " | " | " | " | |
| 918 | NHCH₃ | " | " | " | " | " | |
| 919 | OCH₃ | " | " | N | " | " | |
| 920 | " | " | " | O | " | " | |
| 921 | " | " | " | " | CH cyclopentyl | " | |
| 922 | Cl | " | " | " | " | " | |
| 923 | CH₃ | " | " | " | " | " | |
| 924 | NHCH₃ | " | " | " | " | " | |
| 925 | OCH₃ | " | " | S | " | " | |
| 926 | Cl | " | " | " | " | " | |

TABLE I-continued

| | | | | | |
|---|---|---|---|---|---|
| 927 CH₃ | " | " | " | " | " |
| 928 NHCH₃ | " | " | " | " | " |
| 929 OCH₃ | " | " | N | " | " |
| 930 " | " | O | " | " | " |
| 931 OCH₃ | OCH₃ | O | CH | i-C₃H₇ | OCH₂COON=C(CH₃)₂ |
| 932 Cl | " | " | " | " | " |
| 933 CH₃ | " | " | " | " | " |
| 934 NHCH₃ | " | " | " | " | " |
| 935 OCH₃ | " | S | " | " | " |
| 936 Cl | " | " | " | " | " |
| 937 CH₃ | " | " | " | " | " |
| 938 NHCH₃ | " | " | " | " | " |
| 939 OCH₃ | " | " | N | " | " |
| 940 " | " | O | " | " | " |
| 941 " | " | " | " | t-Bu | " |
| 942 Cl | " | " | " | " | " |
| 943 CH₃ | " | " | " | " | " |
| 944 NHCH₃ | " | " | " | " | " |
| 945 OCH₃ | " | " | " | " | " |
| 946 Cl | " | " | " | " | " |
| 947 CH₃ | " | " | " | " | " |
| 948 NHCH₃ | " | " | " | " | " |
| 949 OCH₃ | " | " | N | " | " |
| 950 " | " | O | " | " | " |
| 951 " | " | " | CH | cyclopentyl | " |
| 952 Cl | " | " | " | " | " |
| 953 CH₃ | " | " | " | " | " |
| 954 NHCH₃ | " | " | " | " | " |
| 955 OCH₃ | " | S | " | " | " |
| 956 Cl | " | " | " | " | " |
| 957 CH₃ | " | " | " | " | " |
| 958 NHCH₃ | " | " | " | " | " |
| 959 OCH₃ | " | " | N | " | " |
| 960 " | " | O | " | " | " |
| 961 OCH₃ | OCH₃ | O | CH | i-C₃H₇ | OCH(CH₃)CON=C(CH₃)₂ |
| 962 Cl | " | " | " | " | " |
| 963 CH₃ | " | " | " | " | " |
| 964 NHCH₃ | " | " | " | " | " |
| 965 OCH₃ | " | S | " | " | " |
| 966 Cl | " | " | " | " | " |
| 967 CH₃ | " | " | " | " | " |
| 968 NHCH₃ | " | " | " | " | " |
| 969 OCH₃ | " | " | N | " | " |
| 970 " | " | O | " | " | " |
| 971 " | " | " | " | t-Bu | " |
| 972 Cl | " | " | " | " | " |
| 973 CH₃ | " | " | " | " | " |
| 974 NHCH₃ | " | " | " | " | " |
| 975 OCH₃ | " | " | " | " | " |
| 976 Cl | " | " | " | " | " |
| 977 CH₃ | " | " | " | " | " |
| 978 NHCH₃ | " | " | " | " | " |
| 979 OCH₃ | " | " | N | " | " |
| 980 " | " | O | " | " | " |
| 981 " | " | " | CH | cyclopentyl | " |
| 982 Cl | " | " | " | " | " |
| 983 CH₃ | " | " | " | " | " |
| 984 NHCH₃ | " | " | " | " | " |
| 985 OCH₃ | " | S | " | " | " |
| 986 Cl | " | " | " | " | " |
| 987 CH₃ | " | " | " | " | " |
| 988 NHCH₃ | " | " | " | " | " |
| 989 OCH₃ | " | " | N | " | " |
| 990 " | " | O | " | " | " |
| 991 OCH₃ | OCH₃ | O | CH | i-C₃H₇ | —NH—CH₂—CO—OCH₂CH=CH₂ |
| 992 Cl | " | " | " | " | " |
| 993 CH₃ | " | " | " | " | " |
| 994 NHCH₃ | " | " | " | " | " |
| 995 OCH₃ | " | S | " | " | " |
| 996 Cl | " | " | " | " | " |
| 997 CH₃ | " | " | " | " | " |
| 998 NHCH₃ | " | " | " | " | " |
| 999 OCH₃ | " | " | N | " | " |
| 1000 " | " | O | " | " | " |
| 1001 " | " | " | " | t-Bu | " |
| 1002 Cl | " | " | " | " | " |
| 1003 CH₃ | " | " | " | " | " |
| 1004 NHCH₃ | " | " | " | " | " |
| 1005 OCH₃ | " | S | " | " | " |
| 1006 Cl | " | " | " | " | " |
| 1007 CH₃ | " | " | " | " | " |
| 1008 NHCH₃ | " | " | " | " | " |

TABLE I-continued

| No. | | | | | | | |
|---|---|---|---|---|---|---|---|
| 1009 | OCH₃ | " | " | N | " | " | |
| 1010 | " | " | O | " | " | " | |
| 1011 | " | " | " | CH | cyclopentyl | " | |
| 1012 | Cl | " | " | " | " | " | |
| 1013 | CH₃ | " | " | " | " | " | |
| 1014 | NHCH₃ | " | " | " | " | " | |
| 1015 | OCH₃ | " | S | " | " | " | |
| 1016 | Cl | " | " | " | " | " | |
| 1017 | CH₃ | " | " | " | " | " | |
| 1018 | NHCH₃ | " | " | " | " | " | |
| 1019 | OCH₃ | " | " | N | " | " | |
| 1020 | " | " | O | " | " | " | |
| 1021 | OCH₃ | OCH₃ | O | CH | i-C₃H₇ | —NH—CH₂CO—OCH₂C≡CH | |
| 1022 | Cl | " | " | " | " | " | |
| 1023 | CH₃ | " | " | " | " | " | |
| 1024 | NHCH₃ | " | " | " | " | " | |
| 1025 | OCH₃ | " | S | " | " | " | |
| 1026 | Cl | " | " | " | " | " | |
| 1027 | CH₃ | " | " | " | " | " | |
| 1028 | NHCH₃ | " | " | " | " | " | |
| 1029 | OCH₃ | " | " | N | " | " | |
| 1030 | " | " | O | " | " | " | |
| 1031 | " | " | " | " | t-Bu | " | |
| 1032 | Cl | " | " | " | " | " | |
| 1033 | CH₃ | " | " | " | " | " | |
| 1034 | NHCH₃ | " | " | " | " | " | |
| 1035 | OCH₃ | " | " | " | " | " | |
| 1036 | Cl | " | " | " | " | " | |
| 1037 | CH₃ | " | " | " | " | " | |
| 1038 | NHCH₃ | " | " | " | " | " | |
| 1039 | OCH₃ | " | " | N | " | " | |
| 1040 | " | " | O | " | " | " | |
| 1041 | " | " | " | CH | cyclopentyl | " | |
| 1042 | Cl | " | " | " | " | " | |
| 1043 | CH₃ | " | " | " | " | " | |
| 1044 | NHCH₃ | " | " | " | " | " | |
| 1045 | OCH₃ | " | S | " | " | " | |
| 1046 | Cl | " | " | " | " | " | |
| 1047 | CH₃ | " | " | " | " | " | |
| 1048 | NHCH₃ | " | " | " | " | " | |
| 1049 | OCH₃ | " | " | N | " | " | |
| 1050 | " | " | O | " | " | " | |
| 1051 | OCH₃ | OCH₃ | O | CH | i-C₃H₇ | —NHCH(CH₃)COSCH₂Ph | |
| 1052 | Cl | " | " | " | " | " | |
| 1053 | CH₃ | " | " | " | " | " | |
| 1054 | NHCH₃ | " | " | " | " | " | |
| 1055 | OCH₃ | " | S | " | " | " | |
| 1056 | Cl | " | " | " | " | " | |
| 1057 | CH₃ | " | " | " | " | " | |
| 1058 | NHCH₃ | " | " | " | " | " | |
| 1059 | OCH₃ | " | " | N | " | " | |
| 1060 | " | " | O | " | " | " | |
| 1061 | " | " | " | " | t-Bu | " | |
| 1062 | Cl | " | " | " | " | " | |
| 1063 | CH₃ | " | " | " | " | " | |
| 1064 | NHCH₃ | " | " | " | " | " | |
| 1065 | OCH₃ | " | " | " | " | " | |
| 1066 | Cl | " | " | " | " | " | |
| 1067 | CH₃ | " | " | " | " | " | |
| 1068 | NHCH₃ | " | " | " | " | " | |
| 1069 | OCH₃ | " | " | N | " | " | |
| 1070 | " | " | O | " | " | " | |
| 1071 | " | " | " | CH | cyclopentyl | " | |
| 1072 | Cl | " | " | " | " | " | |
| 1073 | CH₃ | " | " | " | " | " | |
| 1074 | NHCH₃ | " | " | " | " | " | |
| 1075 | OCH₃ | " | S | " | " | " | |
| 1076 | Cl | " | " | " | " | " | |
| 1077 | CH₃ | " | " | " | " | " | |
| 1078 | NHCH₃ | " | " | " | " | " | |
| 1079 | OCH₃ | " | " | N | " | " | |
| 1080 | " | " | O | " | " | " | |
| 1081 | OCH₃ | OCH₃ | O | CH | i-C₃H₇ | —OCH(t-Bu)(CN) | 90–92 |
| 1082 | Cl | " | " | " | " | " | |
| 1083 | CH₃ | " | " | " | " | " | |
| 1084 | NHCH₃ | " | " | " | " | " | |
| 1085 | OCH₃ | " | S | " | " | " | |
| 1086 | Cl | " | " | " | " | " | |
| 1087 | CH₃ | " | " | " | " | " | |
| 1088 | NHCH₃ | " | " | " | " | " | |
| 1089 | OCH₃ | " | " | N | " | " | |
| 1090 | " | " | O | " | " | " | |

TABLE I-continued

| No. | | | | | | |
|---|---|---|---|---|---|---|
| 1091 | " | " | " | " | t-Bu | " |
| 1092 | Cl | " | " | " | " | " |
| 1093 | CH$_3$ | " | " | " | " | " |
| 1094 | NHCH$_3$ | " | " | " | " | " |
| 1095 | OCH$_3$ | " | " | " | " | " |
| 1096 | Cl | " | " | " | " | " |
| 1097 | CH$_3$ | " | " | " | " | " |
| 1098 | NHCH$_3$ | " | " | " | " | " |
| 1099 | OCH$_3$ | " | " | N | " | " |
| 1100 | " | " | O | " | " | " |
| 1101 | " | " | " | CH | cyclopentyl | " |
| 1102 | Cl | " | " | " | " | " |
| 1103 | CH$_3$ | " | " | " | " | " |
| 1104 | NHCH$_3$ | " | " | " | " | " |
| 1105 | OCH$_3$ | " | S | " | " | " |
| 1106 | Cl | " | " | " | " | " |
| 1107 | CH$_3$ | " | " | " | " | " |
| 1108 | NHCH$_3$ | " | " | " | " | " |
| 1109 | OCH$_3$ | " | " | N | " | " |
| 1110 | " | " | O | " | " | " |
| 1111 | OCH$_3$ | OCH$_3$ | O | CH | i-C$_3$H$_7$ | —OCH(CH$_3$)CN |
| 1112 | Cl | " | " | " | " | " |
| 1113 | CH$_3$ | " | " | " | " | " |
| 1114 | NHCH$_3$ | " | " | " | " | " |
| 1115 | OCH$_3$ | " | S | " | " | " |
| 1116 | Cl | " | " | " | " | " |
| 1117 | CH$_3$ | " | " | " | " | " |
| 1118 | NHCH$_3$ | " | " | " | " | " |
| 1119 | OCH$_3$ | " | " | N | " | " |
| 1120 | " | " | O | " | " | " |
| 1121 | " | " | " | " | t-Bu | " |
| 1122 | Cl | " | " | " | " | " |
| 1123 | CH$_3$ | " | " | " | " | " |
| 1124 | NHCH$_3$ | " | " | " | " | " |
| 1125 | OCH$_3$ | " | " | " | " | " |
| 1126 | Cl | " | " | " | " | " |
| 1127 | CH$_3$ | " | " | " | " | " |
| 1128 | NHCH$_3$ | " | " | " | " | " |
| 1129 | OCH$_3$ | " | " | N | " | " |
| 1130 | " | " | O | " | " | " |
| 1131 | " | " | " | CH | cyclopentyl | " |
| 1132 | Cl | " | " | " | " | " |
| 1133 | CH$_3$ | " | " | " | " | " |
| 1134 | NHCH$_3$ | " | " | " | " | " |
| 1135 | OCH$_3$ | " | S | " | " | " |
| 1136 | Cl | " | " | " | " | " |
| 1137 | CH$_3$ | " | " | " | " | " |
| 1138 | NHCH$_3$ | " | " | " | " | " |
| 1139 | OCH$_3$ | " | " | N | " | " |
| 1140 | OCH$_3$ | OCH$_3$ | O | N | cyclopentyl | —OCH(CH$_3$)CN |
| 1141 | " | " | " | CH | i-Pr | O—Si(CH$_3$)$_2$—C(CH$_3$)$_2$—CH(CH$_3$)$_2$    Öl |

Note: In Table I, Ph = phenyl, Pr = propyl and Bu = butyl.

BIOLOGICAL EXAMPLES

The damage to the weed plants, or the crop plant compatibility, was rated using a key in which the effectiveness is expressed by scores from 0 to 5. In this key, 0 = no action
1 = 0 to 20% action or damage
2 = 20 to 40% action or damage
3 = 40 to 60% action or damage
4 = 60 to 80% action or damage
5 = 80 to 100% action or damage 1. Pre-emergence herbicidal action Seeds or rhizome pieces of mono- and dicotyledon weed plants were placed in plastic pots containing sandy loam soil and covered with soil. Various dosage rates of the compounds according to the invention formulated in the form of wettable powders or emulsion concentrates were then applied to the surface of the soil cover in the form of an aqueous suspension or emulsion at a water application rate of 600 to 800 l/ha (converted).

After the treatment, the pots were placed in the greenhouse and kept under good growth conditions for the weeds. Optical rating of the plant damage, or inadequate emergence, was effected after the test plants had emerged after a trial time of 3 to 4 weeks in comparison with untreated controls. As shown by the score figures in Table 3, the compounds according to the invention have a good herbicidal pre-emergence activity against a broad range of grass weeds and broad-leaf weeds.

TABLE II

| | | Pre-emergence action | | | |
|---|---|---|---|---|---|
| | Dosage rate | Herbicidal action | | | |
| Ex. No. | (kg of a.i./ha) | STAL | STME | ECCR | LOMU |
| 31 | 1.25 | 5 | 5 | 5 | 5 |
| 181 | 0.3 | 5 | 5 | 5 | 5 |
| 211 | 0.3 | 5 | 5 | 5 | 5 |
| 1 | 0.3 | 5 | 5 | 5 | 5 |

TABLE II-continued

| | | Pre-emergence action | | | |
|---|---|---|---|---|---|
| | Dosage rate | Herbicidal action | | | |
| Ex. No. | (kg of a.i./ha) | STAL | STME | ECCR | LOMU |
| 571 | 0.3 | 5 | 5 | 5 | 5 |
| 361 | 0.3 | 5 | 5 | 5 | 5 |
| 391 | 0.3 | 5 | 5 | 4 | 4 |
| 511 | 0.3 | 5 | 5 | 5 | 5 |

Abbreviations:
STAL = *Sinapis alba*
STME = *Stellaria media*
ECCR = *Echinochloa crus-galli*
LOMU = *Lolium multiflorum*
a.i. = active ingredient 2. Post-emergence herbicidal action Seeds or rhizome pieces of mono- and dicotyledon weeds were placed in plastic pots containing sandy loam soil, covered with soil and grown in the greenhouse under good growth conditions. Three weeks after sowing, the test plants were treated at the three-leaf stage.

Various dosage rates of the compounds according to the invention formulated as wettable powders or emulsion concentrates were sprayed on the green parts of the plants at a water application rate of 600 to 800 l/ha (converted), and, after the test plants had remained in the greenhouse for approx. 3 to 4 weeks under ideal growth conditions, the action of the preparations was scored visually in comparison rated with untreated controls.

The compositions according to the invention also have a good herbicidal activity against a broad range of economically important grass weeds and broad-leaf weeds when used post-emergence.

TABLE III

| | | Post-emergence action | | | |
|---|---|---|---|---|---|
| | Dosage rate | Herbicidal action | | | |
| Ex. No. | (kg of a.i./ha) | STAL | STME | ECCR | LOMU |
| 31 | 1.25 | 5 | 5 | 5 | 5 |
| 181 | 0.3 | 5 | 5 | 5 | 5 |
| 211 | 0.3 | 5 | 4 | 5 | 5 |
| 1 | 0.3 | 5 | 5 | 5 | 5 |
| 571 | 0.3 | 4 | 4 | 3 | 5 |
| 361 | 0.3 | 5 | 5 | 5 | 5 |
| 391 | 0.3 | 5 | 5 | 4 | 4 |
| 511 | 0.3 | 5 | 5 | 5 | 5 |

Abbreviations: as in Table II

We claim:

1. A compound of the formula (I)

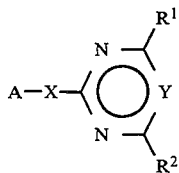

(I)

in which

A is a radical formula

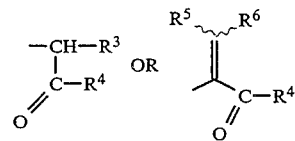

X is O or S,
Y is CH,
$R^1$, $R^2$ independently of one another are $C_1$–$C_4$-alkyl, $C_1$–$C_4$-alkoxy, halogen, $C_1$–$C_4$-haloalkoxy, $C_1$–$C_4$-alkylamino or di-($C_1$–$C_4$-alkyl)amino,
$R^3$ is isopropyl, tert-butyl or cyclopentyl,
$R^4$ is a $C_1$–$C_4$-alkoxy radical which is substituted by $C_2$–$C_4$-alkenyloxy, $C_2$–$C_4$-alkinyloxy, cyclohexyloxy, cyclohexenyloxy, cyclopentyloxy, cyclopentenyloxy, benzyloxy, benzylthio, $(R^*)_3Si$ or $(R^*)_3SiO$, in which the radicals $R^*$ independently of one another are $C_1$–$C_4$-alkyl, $C_2$–$C_4$-alkenyl, $C_2$–$C_4$-alkinyl or phenyl, or by cyano, nitro, ($C_1$–$C_4$-alkyl)-carbonyl, $C_1$–$C_4$-alkylsulfonyl, $C_1$–$C_4$-alkylsulfinyl, di ($C_1$–$C_4$-alkyl)-phosphoryl, di-($C_1$–$C_4$-alkyl)-phosphonyl, di-($C_1$–$C_4$-alkyl)-phosphinyl or pyridyl, or is a radical of a 5- or 6-membered cyclic lactone bonded through the carbon in the α-position relative to the carbonyl group, or, $R^4$ is a radical of the formula $$-D^7-CR^{15}R^{16}-L$$

in which
$D^7$ is O, S, NH, methylamino or ethylamino,
$R^{15}$, $R^{16}$ independently of one another are hydrogen, $C_1$–$C_4$-alkyl, $C_2$–$C_4$-alkenyl, $C_2$–$C_4$-alkinyl, phenyl or benzyl,
L is an acid derivative radical of the formula $$-CO-O-R^{17}$$

$$-CO-S-R^{18}$$

$$-CO-NR^{19}R^{20}$$

$$-CO-O-N=CR^{21}R^{22}$$

$$-CO-N=CR^{21}R^{22}$$

$$-O-CO-R^{23}$$

$$-S-CO-R^{23}$$

$$-NR^{14}-CO-R^{23}$$

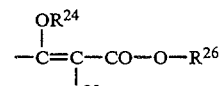

or

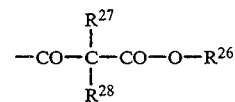

$R^{17}$ is hydrogen, $C_2$–$C_4$-alkenyl or $C_2$–$C_4$-alkinyl, cyclohexyl, cyclopentyl, cyclohexenyl, cyclopentenyl, benzyl, phenyl or phenyl substituted by one or more radicals selected from the group consisting of halogen, $C_1$–$C_4$-alkyl, $C_1$–$C_4$-alkoxy, $C_1$–$C_4$-haloalkyl, $C_1$–$C_4$-haloalkoxy, nitro and cyano, $R^{18}$ is hydrogen, $C_1$–$C_4$-alkyl, $C_2$–$C_4$-alkenyl or $C_2$–$C_4$-alkinyl, cyclohexyl, cyclopentyl, cyclohexenyl, cyclopentenyl, benzyl, phenyl or phenyl substituted by one or more radicals selected from the group consisting of halogen, $C_1$–$C_4$-alkyl, $C_1$–$C_4$-alkoxy, $C_1$–$C_4$haloalkyl, $C_1$–$C_4$-haloalkoxy, nitro and cyano, $R^{19}$, $R^{20}$ independently of one another are hydrogen, $C_1$–$C_4$-alkyl, $C_2$–$C_4$-alkenyl, $C_2$–$C_4$-alkinyl, cyclohexyl, cyclopentyl, benzyl, phenyl or phenyl substituted by one or more radicals selected from the group consisting of halogen, $C_1$–$C_4$-alkyl, $C_1$–$C_4$-alkoxy, $C_1$–$C_4$-haloalkyl, $C_1$–$C_4$-haloalkoxy, nitro and cyano, or together with the nitrogen atom linking them, are a heterocyclic 5- or 6-membered ring, $R^{21}$, $R^{22}$ independently of one another are $C_1$–$C_4$-alkyl, $C_2$–$C_4$-alkenyl or $C_2$–$C_4$-alkinyl or together with the carbon atom linking them, a carbocyclic 5- or 6- membered ring, $R^{23}$ is hydrogen, $C_1$–$C_4$-alkyl, cyclohexyl, cyclopentyl, phenyl or phenyl substituted by one or more radicals selected from the group consisting of halogen, $C_1$–$C_4$-alkyl, $C_1$–$C_4$-alkoxy, $C_1$–$C_4$-haloalkyl, $C_1$–$C_4$-haloalkoxy, nitro and cyano, $R^{24}$ is $C_1$–$C_4$-alkyl, $C_2$–$C_4$-alkenyl or $C_2$–$C_4$-alkinyl, where the last-mentioned 3 radicals are unsubstituted or substituted by one or more radicals from the group consisting of halogen or $C_1$–$C_4$-alkoxy, or is $C_1$–$C_4$-alkanoyl, ($C_1$–$C_4$-alkoxy)-carbonyl, benzyl, benzoxycarbonyl, phenyl or benzoyl, where the last-membered 4 radicals are unsubstituted or substituted by $C_1$–$C_4$-alkyl, $C_1$–$C_4$-alkoxy, halogen or nitro, $R^{25}$ hydrogen or $C_1$–$C_4$-alkyl, $R^{26}$ is hydrogen, $C_1$–$C_4$-alkyl, $C_2$–$C_4$-alkenyl or $C_2$–$C_4$-alkinyl, where the last-mentioned 3 radicals are unsubstituted or substituted by one or more halogen atoms $R^{27}$, $R^{28}$ independently of one another are hydrogen or $C_1$–$C_4$-alkyl, or $R^4$ is a radical of the formula

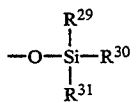

where $R^{29}$, $R^{30}$, $R^{31}$ independently of one another are $C_1$–$C_4$-alkyl, $C_2$–$C_4$-alkenyl $C_2$–$C_4$-alkinyl, phenyl or phenyl substituted by one or more radicals selected from the group consisting of halogen, $C_1$–$C_4$-alkyl, $C_1$–$C_4$-alkoxy, $C_1$–$C_4$-haloalkyl, $C_1$–$C_4$-haloalkoxy, nitro and cyano, $R^5$ is $C_1$–$C_4$-alkyl, $C_2$–$C_4$-alkenyl or $C_2$–$C_4$-alkinyl, cyclohexyl, cyclopentyl, phenyl, pyridyl or thienyl, where the 3 last-mentioned radicals are unsubstituted or substituted by 1 to 3 radicals Z, $R^6$ is hydrogen or $C_1$–$C_4$-alkyl, and Z is halogen, $C_1$–$C_4$-alkyl, $C_1$–$C_4$-haloalkyl, $C_1$–$C_4$-haloalkoxy, $C_1$–$C_4$-alkylthio, $C_1$–$C_4$-alkylamino, di-($C_1$–$C_4$-alkyl)-amino or nitro.

2. A compound as claimed in claim 1 wherein $R^4$ is a $C_1$–$C_4$-alkoxy radical which is substituted by allyloxy, propargyloxy, (R*)$_3$Si or (R*)$_3$SiO, in which the radicals R* independently of one another are methyl, ethyl or phenyl, or by $C_1$–$C_4$-alkylsulfonyl, $C_1$–$C_4$-alkylsulfinyl, di-($C_1$–$C_4$-alkyl)-phosphinyl, di-($C_1$–$C_4$-alkyl)-phosphonyl or di-($C_1$–$C_4$-alkyl)-phosphoryl, or is a radical of a 5- or 6-membered cyclic lactone bonded through the carbon in the α-position relative to the carbonyl group, or $R^4$ is a radical of the formula

$D^7$ is O, S or NH, $R^{15}$, $R^{16}$ independently of one another are hydrogen or methyl, L is an acid derivative radical of the formula

—CO—O—$R^{17}$

—CO—S—$R^{18}$

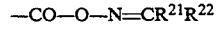

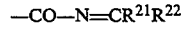

—O—CO—$R^{23}$

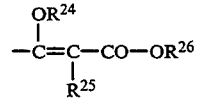

or

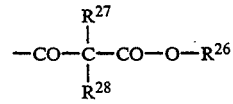

or $R^{17}$ is hydrogen, $C_2$–$C_4$-alkenyl or $C_2$–$C_4$alkinyl, benzyl or phenyl, $R^{18}$ is hydrogen, $C_1$–$C_4$-alkyl, $C_2$–$C_4$-alkenyl or $C_2$–$C_4$-alkinyl, benzyl or phenyl, $R^{19}$, $R^{20}$ independently of one another are hydrogen, $C_1$–$C_4$-alkyl, $C_2$–$C_4$-alkenyl, $C_2$–$C_4$-alkinyl, cyclohexyl, cyclopentyl, benzyl, phenyl or phenyl substituted by one or more radicals selected from the group consisting of halogen, $C_1$–$C_4$-alkyl, $C_1$–$C_4$-alkoxy, $C_1$–$C_4$-haloalkyl, $C_1$–$C_4$-haloalkoxy, nitro and cyano, or together with the nitrogen atom linking them, a heterocyclic 5- or 6-membered ring, $R^{24}$ is $C_1$–$C_4$-alkyl, which is unsubstituted or substituted by one or more radicals selected from the group consisting of halogen, and $C_1$–$C_4$-alkoxy, or is ($C_1$–$C_4$-alkoxy)-carbonyl, benzyl, benzoxycarbonyl, phenyl or benzoyl, where the last-mentioned 4 radicals are unsubstituted or substituted by $C_1$–$C_4$-alkyl, $C_1$–$C_4$-alkoxy, halogen or nitro, $R^{25}$ is hydrogen or $C_1$–$C_4$-alkyl, $R^{26}$ is hydrogen, $C_1$–$C_4$-alkyl, $C_2$–$C_4$-alkenyl or $C_2$–$C_4$-alkinyl, and $R^{27}$, $R^{28}$ independently of one another are hydrogen or $C_1$–$C_4$-alkyl, or $R^4$ is a radical of the formula

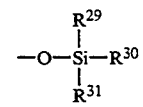

where $R^{29}$, $R^{30}$, $R^{31}$ independently of one another are $C_1$-$C_4$-alkyl, $C_2$-$C_4$-alkenyl, $C_2$-$C_4$-alkinyl or phenyl.

3. A compound as claimed in claim 2, wherein
$R^4$ is a $C_1$-$C_4$-alkoxyl radical which is substituted by allyloxy, propargyloxy, $(R_*)_3Si$ or $(R^*)_3SiO$, in which the radicals $R^*$ independently or one another are methyl, ethyl or phenyl, or by $C_1$-$C_4$-alkysulfonyl, $C_1$-$C_4$-alkylsulfinyl, di-($C_1$-$C_4$-alkyl)-phosphinyl, di-$C_1$-$C_4$-alkyl)-phosphonyl or di-($C_1$-$C_4$-alkyl)-phosphoryl, or is the radical of a 5- or 6-membered cyclic lactone bonded through the carbon in the α-position relative to the carbonyl group, or $R^4$ is a radical of the formula

—D—CR$^{15}$R$^{16}$—L $D^7$ is O, S or NH,
$R^{15}$, $R^{16}$ independently of one another are hydrogen or methyl, L is an acid derivative radical of the formula

—CO—O—R$^{17}$

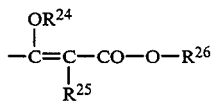

or

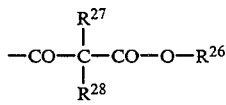

$R^{17}$ is hydrogen, $C_2$-$C_4$-alkenyl or $C_2$-$C_4$-alkinyl, benzyl or phenyl,
$R^{24}$ is $C_1$-$C_4$-alkyl, which is unsubstituted or substituted by one or more radicals selected from the group consisting of halogen and $C_1$-$C_4$-alkoxy, or is ($C_1$-$C_4$-alkoxy)-carbonyl, benzyl, benzoxycarbonyl, phenyl or benzoyl, where the last-mentioned 4 radicals are unsubstituted or substituted by $C_1$-$C_4$-alkyl, $C_1$-$C_4$-alkoxy, halogen or nitro,
$R^{25}$ is hydrogen or $C_1$-$C_4$-alkyl,
$R^{26}$ is hydrogen, $C_1$-$C_4$-alkyl, $C_2$-$C_4$-alkenyl or $C_2$-$C_4$-alkinyl, and
$R^{27}$, $R^{28}$ independently of one another are hydrogen or $C_1$-$C_4$-alkyl.

4. A compound as claimed in claim 3, wherein
X is O,
$R^1$, $R^2$ independently of one another are $C_1$-$C_4$-alkyl or $C_1$-$C_4$-alkoxy,
$R^3$ is isopropyl, tert-butyl or cyclopentyl,
$R^4$ is a $C_1$-$C_4$-alkoxy radical which is substituted by allyloxy, propargyloxy, $(R^*)_3Si$ or $(R^*)_3SiO$, in which the radicals $R^*$ independently of one another are methyl or ethyl, or by $C_1$-$C_4$-alkylsulfonyl, di-($C_1$-$C_4$-alkyl)phosphonyl, or
is 2-oxo-1-oxolan-3-yl
or
is a radical of the formula

—D$^7$—CR$^{15}$R$^{16}$—L $D^7$ is O,
$R^{15}$, $R^{16}$ independently of one another are hydrogen or methyl
L is an acid derivative radical of the formula

CO—O—R$^{17}$

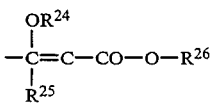

or

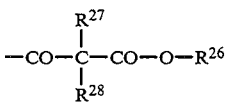

$R^{17}$ is hydrogen, allyl, propargyl or benzyl,
$R^{24}$ is $C_1$-$C_4$-alkyl,
$R^{25}$ is hydrogen or $C_1$-$C_4$-alkyl
$R^{26}$ is hydrogen, $C_1$-$C_4$-alkyl, $C_2$-$C_4$-alkenyl or $C_2$-$C_4$-alkinyl, and
$R^{27}$, $R^{28}$ independently of one another are hydrogen or methyl.

5. A compound as claimed in claim 2, wherein
$R^4$ is a radical of the formula

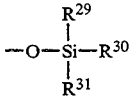

where
$R^{29}$, $R^{30}$, $R^{31}$ independently of one another are $C_1$-$C_4$-alkyl, $C_2$-$C_4$-alkenyl, $C_2$-$C_4$-alkinyl or phenyl.

6. A compound as claimed in claim 2, wherein $R^{29}$, $R^{30}$, $R^{31}$ independently of one another are $C_1$-$C_4$-alkyl.

7. A herbicidal or plant growth-regulating composition which comprises an effective amount of a compound of formula (I) as defined in claim 1, and conventional formulation auxiliaries.

8. A method for controlling harmful plants or for regulating the growth of plants, which comprises applying an effective amount of one or more compounds of formula (I) as claimed in claim 1, to the plants, seeds of the plants or the area under cultivation.

* * * * *